(12) United States Patent
Fu

(10) Patent No.: US 10,080,506 B2
(45) Date of Patent: *Sep. 25, 2018

(54) METHOD FOR PROCESSING BRAINWAVE SIGNALS

(71) Applicant: Chi Yung Fu, Oakland, CA (US)

(72) Inventor: Chi Yung Fu, Oakland, CA (US)

( * ) Notice: Subject to any disclaimer, the term of this patent is extended or adjusted under 35 U.S.C. 154(b) by 212 days.

This patent is subject to a terminal disclaimer.

(21) Appl. No.: 14/814,364

(22) Filed: Jul. 30, 2015

(65) Prior Publication Data

US 2015/0327813 A1 Nov. 19, 2015

Related U.S. Application Data

(63) Continuation of application No. 12/804,939, filed on Aug. 2, 2010, now Pat. No. 9,095,266.

(51) Int. Cl.
*A61B 5/04* (2006.01)
*A61B 5/0476* (2006.01)
(Continued)

(52) U.S. Cl.
CPC .......... *A61B 5/0476* (2013.01); *A61B 5/0042* (2013.01); *A61B 5/0075* (2013.01);
(Continued)

(58) Field of Classification Search
CPC .......... A61B 5/0476; A61B 2560/0214; A61B 2562/046; A61B 2562/14;
(Continued)

(56) References Cited

U.S. PATENT DOCUMENTS 4,753,246 A 6/1988 Freeman
4,949,726 A 8/1990 Hartzell et al.
(Continued)

FOREIGN PATENT DOCUMENTS

WO 2007141325 A1 12/2007
WO 2009107069 A2 9/2009
(Continued)

OTHER PUBLICATIONS

Non-Final Office Action dated Sep. 26, 2017 in U.S. Appl. No. 14/715,498.
(Continued)

*Primary Examiner* — Amanda Hulbert
(74) *Attorney, Agent, or Firm* — Perkins Coie LLP; Alberto Araiza; Viola T. Kung

(57) ABSTRACT

A signal processing method and system combines multi-scale decomposition, such as wavelet, pre-processing together with a compression technique, such as an auto-associative artificial neural network, operating in the multi-scale decomposition domain for signal denoising and extraction. All compressions are performed in the decomposed domain. A reverse decomposition such as an inverse discrete wavelet transform is performed on the combined outputs from all the compression modules to recover a clean signal back in the time domain. A low-cost, non-drug, non-invasive, on-demand therapy braincap system and method are pharmaceutically nonintrusive to the body for the purpose of disease diagnosis, treatment therapy, and direct mind control of external devices and systems. It is based on recognizing abnormal brainwave signatures and intervenes at the earliest moment, using magnetic and/or electric stimulations to reset the brainwaves back to normality. The feedback system is self-regulatory and the treatment stops when the brainwaves return to normal. The braincap contains multiple sensing electrodes and microcoils; the microcoils are pairs of crossed microcoils or 3-axis triple crossed microcoils.

32 Claims, 22 Drawing Sheets

(51) Int. Cl.

| | | |
|---|---|---|
| *A61N 1/04* | (2006.01) | |
| *A61B 5/00* | (2006.01) | |
| *A61N 2/00* | (2006.01) | |
| *A61N 1/36* | (2006.01) | |
| *A61B 5/0402* | (2006.01) | |
| *A61N 5/10* | (2006.01) | |
| *A61N 5/02* | (2006.01) | |
| *A61N 1/40* | (2006.01) | |
| *A61N 7/00* | (2006.01) | |
| *A61B 5/0484* | (2006.01) | |
| *A61N 2/02* | (2006.01) | |
| *A61B 5/0478* | (2006.01) | |
| *G06F 19/00* | (2018.01) | |
| *G16H 50/20* | (2018.01) | |
| *A61N 1/05* | (2006.01) | |
| *A61B 5/16* | (2006.01) | |

(52) U.S. Cl.
CPC ........ *A61B 5/0402* (2013.01); *A61B 5/04009* (2013.01); *A61B 5/04012* (2013.01); *A61B 5/0478* (2013.01); *A61B 5/0484* (2013.01); *A61B 5/4836* (2013.01); *A61B 5/6803* (2013.01); *A61B 5/7203* (2013.01); *A61N 1/0408* (2013.01); *A61N 1/0476* (2013.01); *A61N 1/36014* (2013.01); *A61N 1/36021* (2013.01); *A61N 1/36025* (2013.01); *A61N 1/40* (2013.01); *A61N 2/006* (2013.01); *A61N 2/008* (2013.01); *A61N 2/02* (2013.01); *A61N 5/02* (2013.01); *A61N 5/10* (2013.01); *A61N 7/00* (2013.01); *G06F 19/3481* (2013.01); *G16H 50/20* (2018.01); *A61B 5/165* (2013.01); *A61B 5/726* (2013.01); *A61B 5/7264* (2013.01); *A61B 2560/0214* (2013.01); *A61B 2562/046* (2013.01); *A61B 2562/14* (2013.01); *A61B 2576/026* (2013.01); *A61N 1/0456* (2013.01); *A61N 1/0526* (2013.01)

(58) Field of Classification Search
CPC ............ A61B 2576/026; A61B 5/0042; A61B 5/0075; A61B 5/04009; A61B 5/04012; A61B 5/0402; A61B 5/0478; A61B 5/0484; A61B 5/165; A61B 5/483; A61N 1/0408; G06N 3/08
USPC ............................................ 607/45; 600/544
See application file for complete search history.

(56) References Cited

U.S. PATENT DOCUMENTS

| | | |
|---|---|---|
| 4,974,587 A | 12/1990 | Turner et al. |
| 5,827,195 A | 10/1998 | Lander |
| 6,016,449 A | 1/2000 | Fischell et al. |
| 6,088,475 A | 7/2000 | Nagashima et al. |
| 6,132,361 A | 10/2000 | Epstein et al. |
| 6,443,883 B1 | 9/2002 | Ostrow et al. |
| 6,587,706 B1 | 7/2003 | Viswanathan |
| 6,763,339 B2 | 7/2004 | Fu et al. |
| 6,898,582 B2 | 5/2005 | Lange |
| 6,976,046 B2 | 12/2005 | Guevorkian et al. |
| 6,983,184 B2 | 1/2006 | Price |
| 7,054,453 B2 | 5/2006 | Causevic et al. |
| 7,099,714 B2 | 8/2006 | Houben |
| 7,186,209 B2 | 3/2007 | Jacobson et al. |
| 7,320,664 B2 | 1/2008 | Riehl et al. |
| 7,519,488 B2 | 4/2009 | Fu et al. |
| 7,647,098 B2 | 1/2010 | Prichep |
| 7,676,263 B2 | 3/2010 | Harris et al. |
| 8,690,748 B1 | 4/2014 | Fu |
| 8,725,669 B1 | 5/2014 | Fu |
| 9,037,224 B1 | 5/2015 | Fu |
| 9,095,266 B1 | 8/2015 | Fu |
| 2002/0007128 A1 | 1/2002 | Ives et al. |
| 2002/0023066 A1 | 2/2002 | Fu et al. |
| 2003/0028072 A1 | 2/2003 | Fischell et al. |
| 2003/0181821 A1 | 9/2003 | Greenwald et al. |
| 2003/0185408 A1 | 10/2003 | Causevic et al. |
| 2004/0138578 A1 | 7/2004 | Pineda et al. |
| 2005/0129775 A1 | 6/2005 | Lanphere et al. |
| 2005/0265629 A1 | 12/2005 | Fu et al. |
| 2006/0200035 A1 | 9/2006 | Ricci et al. |
| 2007/0038382 A1 | 2/2007 | Keenan |
| 2008/0119900 A1 | 5/2008 | Diiorenzo |
| 2008/0208072 A1 | 8/2008 | Fadem et al. |
| 2008/0306325 A1 | 12/2008 | Burnett et al. |
| 2009/0082690 A1 | 3/2009 | Phillips et al. |
| 2009/0099474 A1 | 4/2009 | Pineda et al. |
| 2009/0306454 A1 | 12/2009 | Cockerham et al. |
| 2011/0319975 A1 | 12/2011 | Ho et al. |
| 2012/0150545 A1 | 6/2012 | Simon |

FOREIGN PATENT DOCUMENTS

| | | |
|---|---|---|
| WO | 2010078441 A2 | 7/2010 |
| WO | 2010100643 A2 | 9/2010 |

OTHER PUBLICATIONS

Figueredo et al. Compression of Electrocardiogram Using Neural Networks and Wavelets. Computer and Information Science Studies in Computational Intelligence. vol. 131 (2008); pp. 27-40.

Cvetkovic et al. Automated ELF magnetic field stimulation of human EEG activity. Integrated Computer-Aided Engineering. vol. 13 (2006); pp. 313-328.

METHOD FOR PROCESSING BRAINWAVE SIGNALS

CROSS-REFERENCE TO RELATED APPLICATION

This application is a continuation application of U.S. application Ser. No. 12/804,939, filed Aug. 2, 2010; which has been issued as U.S. Pat. No. 9,095,266; the contents of the above application are incorporated by reference in its entirety.

FIELD OF THE INVENTION

The present invention relates to signal processing, and more particularly to a signal processing method and system for the extraction of signals of unknown or unspecified form or features with severe noise corruption, such as MEG or EEG signals. The invention also relates to generating desired responses to the detected clean signals, in particular to medical diagnostic and treatment methods and apparatus, and more particularly to detection and treatment of mental/neurological conditions.

BACKGROUND OF THE INVENTION

Sensors or instrumentation deployed in real-world settings for various fields, e.g. analytical medicine, and using various detection modalities, e.g. electroencephalography, sonography, and electrocardiography, usually produce signals corrupted by various types of noise. As a result, noise removal is paramount for accurate data extraction, analysis, and interpretation, as well as efficient storage/transmission. For example, noisy data would make data compression much harder and thus affect storage and transmission, e.g. storing X-rays and mammograms. If not done correctly, the typical preprocessing inherent in any instrument design can actually remove valuable information, and subsequent use of even advanced signal processing methods, no matter how capable, will not be able to recover signal lost by inadequate pre-processing. An example of a signal processing system and method using both wavelets and neural network processing is disclosed in U.S. Pat. No. 6,763,339. Signal denoising is performed using wavelet processing which incorporates automatic thresholding methods followed by using a single neural network for shape-matching to extract all relevant patterns. In that technique, the neural network processing is performed in the time domain, and a single neural network is used to extract all the patterns and therefore must be pre-trained to recognize all relevant patterns.

Another example of a signal processing system and method using both wavelets and neural network processing is disclosed in published U.S. Patent Application No. US2005/0265629. Extraction of signals is performed using wavelet processing and supervised neural networks such as a modified Logicon projection system. Clean signals, either theoretical behavior derived from the fundamental physics of first principle or noise free signals obtained by other means such as from shielding all the noise from the signal, are used as the targets for training in the neural networks. Artificial noise such as white noise is then injected into the clean signals to produce synthetic noisy inputs. The noisy inputs and the targeted clean signals are then used as input-output pairs under supervision to train the neural network to recognize the signal from the noisy synthetic inputs. As a result, the system is designed based on artificially created signals instead of real signals. Thus obtaining clean signals is needed. In addition to prior knowledge of the ideal clean signals, the system is trained using only a portion of the signals at a time instead of the entire signal to reduce hardware complexity.

Much equipment that generates signals has an expected signal behavior that one can derive from fundamental physics of first principle. For example, the theoretical signals from gas chromatography should be of Gaussian shape. This known ideal behavior of the signal allows supervised training for the neural networks since the target ideal signal has known and established behavior of Gaussian shape. However, there are signals that are of unknown or unspecific nature or shapes because we do not know the theoretical expected behavior. Some examples are the signals from the human brain. Magnetoencephalography or MEG and Electroencephalography or EEG signals from the brain are highly complex and at this junction our understanding of the brain is incomplete and thus we do not have a theoretical expected signal behavior from the brain. As a result, any neural network based on supervised training is useless since we really do not know the real target signal for it cannot be derived from first principle. What is needed therefore is an efficient and broadly based signal denoising and extraction technique applicable to more generalize signals of unknown or unspecific shapes for better signal detection than for specified signals with known shapes such as signals from gas chromatography.

Neurological/mental disorders have received far less attention than traditional illnesses such as stroke, cancer, and diabetes but they are no less disabling. Treating neurological/mental disorders is essentially based on pharmacotherapy and psychotherapy approaches. In certain cases, surgical interventions have been used.

All drugs have undesirable side effects and relative risks. The psychotropic agents used to treat many neurological/mental illnesses belong to a complex and heterogeneous group of compounds notorious for their unpredictable effects. Antidepressants, adrenergic inhibitors, anti-anxiety agents, anti-kindling agents/mood stabilizers, anticonvulsants, and anti-psychotics drugs used for treatment are no exception. For example, the widely prescribed selective serotonin reuptake inhibitors or SSRI antidepressants are considered to be well tolerated; but approximately 25% of depressed patients in the general population will stop treatment due to intolerable side effects. Drug interactions are another important consideration with these medications. SSRI can inhibit the metabolism of many other medications, while anticonvulsants often have the opposite effect, inducing the activity of liver enzymes and accelerating the metabolism of concurrent drugs.

Regarding psychotherapy, methodological studies, which typically examine cognitive or behavioral treatments, indicate that it does help to relieve severity of symptoms. However, there is no consistent information about whether these interventions are helpful in improving other domains of impairment and associated disability, even though these problems are often the greatest concern to patients; nor does the available evidence specify when, and for whom, various psychotherapeutic interventions should be provided, or whether different treatment modalities can and should be combined, or how they should be combined. Thus psychotherapy is as much an art as a science.

Clearly, alternative approaches other than pharmacotherapy, psychotherapy, and surgeries are needed to address these pressing medical problems.

Repetitive Transcranial Magnetic Stimulation (rTMS) has shown some success for treating comorbid PTSD and major depression. rTMS uses very strong magnetic fields, on the order of one Tesla, to stimulate the brain. The exact mechanism of how the magnetic field affects the brain is not fully known. One possibility is that the alternative magnetic field induces eddy current which then stimulates the brain through excitation or inhibitory effects. It is also possible that the magnetic field or more likely the induced eddy current polarizes or depolarizes the neurons. One medical hypothesis is that the higher frequency (>5 Hz) excites the neurons and the lower frequency (<1 Hz) inhibits the neurons and that the combination of the two creates a Ying and Yan effect. However, very little research has been pursued using dual frequencies (low and high), possibly because the size of the coil makes it hard to have two coils operating simultaneously. For most current Transcranial Magnetic Stimulation (TMS) work, the double-loop coil used measures 174 mm—almost the size of a human head, which may make it difficult to localize the stimulated region of the brain.

SUMMARY OF THE INVENTION

An aspect of the present invention includes a signal processing method comprising: receiving a signal corrupted with noise; decomposing the signal into a plurality of signal components using multi-scale decomposition; inputting each of the plurality of decomposed signal components into a corresponding compression module to squeeze out noise in the signal components in the transform domain; and performing an inverse decomposition on the outputs from all the compression modules to recover a clean signal in the time domain.

Another aspect of the present invention includes a signal processing method comprising: receiving a signal corrupted with noise; performing an n-level decomposition of said signal using a discrete wavelet transform to produce a smooth component and a rough component for each decomposition level; inputting at least the $n^{th}$ level smooth component into a corresponding auto-associative neural network to squeeze out noise in said component in the wavelet domain; and performing an inverse discrete wavelet transform on the output(s) from the auto-associative neural network(s) to recover a clean signal in the time domain.

A further aspect of the present invention includes a system comprising: a signal decomposer for decomposing a signal into a plurality of components of different scale; at least one compression module operatively coupled to the signal decomposer to receive a corresponding component, and to squeeze out noise in the decomposed domain from the corresponding component; and an inverse decomposer capable of recovering a clean signal in the time domain from the combined outputs of the at least one compression module.

Another aspect of the present invention includes a system comprising: a discrete wavelet transformer capable of iteratively decomposing a signal into a plurality of decomposition levels, each having a smooth component and a rough component; at least one auto-associative neural network, each auto-associative neural network operatively coupled to the discrete wavelet transformer to receive a corresponding pre-selected component, and to squeeze out noise in the wavelet domain from a corresponding pre-selected component through constraining the number of neurons in the hidden layer; and an inverse discrete wavelet transformer capable of recovering a clean signal in the time domain from the combined outputs of the plurality of neural networks.

A further aspect of the invention includes a method for treating a patient for certain neurological/mental disorders, comprising: measuring brainwave signals from the patient, the signals being corrupted with noise; processing the measured brainwave signals to obtain clean brainwave signals; matching the clean brainwave signals to a database of brainwave signals for neurological/mental conditions to identify the patient's mental status; and applying therapeutic treatment to the patient based on the identified condition.

Yet another aspect of the invention includes apparatus for treating a patient for certain neurological/mental disorders, comprising: a signal measurement module for measuring brainwave signals from the patient, the signals being corrupted with noise; a signal cleanup module for processing the measured brainwave signals to obtain clean brainwave signals; a signal matching module for matching the clean brainwave signals to a database of brainwave signals for neurological/mental conditions to identify the patient's mental status; and a therapy signal application module for applying therapeutic treatment to the patient based on the identified condition.

Yet a further aspect of the invention includes apparatus for measurement and treatment of neurological and mental conditions of a patient, comprising: a head cap; a plurality of microelectrodes mounted in the cap; and a plurality of pairs of cross-coupled microcoils mounted in the cap.

Another aspect of the invention includes apparatus for treating a patient for certain neurological/mental disorders, comprising: means for measuring brainwave signals from the patient, the signals being corrupted with noise; means for processing the measured brainwave signals to obtain clean brainwave signals; means for matching the clean brainwave signals to a database of brainwave signals for neurological/mental conditions to identify the patient's mental status; and means for applying therapeutic treatment to the patient based on the identified condition.

BRIEF DESCRIPTION OF THE DRAWINGS

The accompanying drawings, which are incorporated into and form a part of the disclosure, are as follows.

DETAILED DESCRIPTION OF THE PREFERRED EMBODIMENTS

Generally, the present invention is directed to a signal processing method and system capable of extracting very low level signals embedded in high levels of noise from a signal of unknown features. In particular, the present invention is a denoising and signal extraction technique based on a combination of multi-scale decomposition and compression technologies with one compression-module for processing a corresponding scale in the decomposed domain. The decomposition generally serves to segment the data into smaller subsets, i.e. decomposed components, each of a different size scale. By using one or more of the decomposed components for subsequent processing, the signal may be separated from the noise coming from various sources. Furthermore, within each scale of the decomposed components, the embedded noise for that scale should be smaller than the entirety of the noise and thus lends itself better for noise removal. As a result, the use of multiple compression modules serves to separately process, i.e. filter by squeezing the noise out, the decomposed components for maximizing system performance. Such a divide and conquer technique enables a more effective signal extraction technique, and addresses the issue of overburdening a single set of decomposed and compression module to extract all the patterns. Further denoising could also be done by setting certain thresholds for each of the decomposed components.

Specifically, upon receiving a signal such as an electroencephalogram (EEG) or a magnetoencephalogram (MEG), corrupted with noise, an n-level decomposition of the signal is performed, such as by using an n-level discrete wavelet transform, to produce various components. In the case of wavelet processing, a smooth component and a rough component will result from each decomposition level. The $n^{th}$ level smoothest component is then input into a corresponding compression module, such as a self-supervised auto-associative neural network, to filter out noise in that component by compressing the transformed signal in the wavelet domain. Additional rough components, beginning at the highest level, may also be retained and input into corresponding additional compression modules to filter out noise in those components, also by signal compression.

Figure 1A:
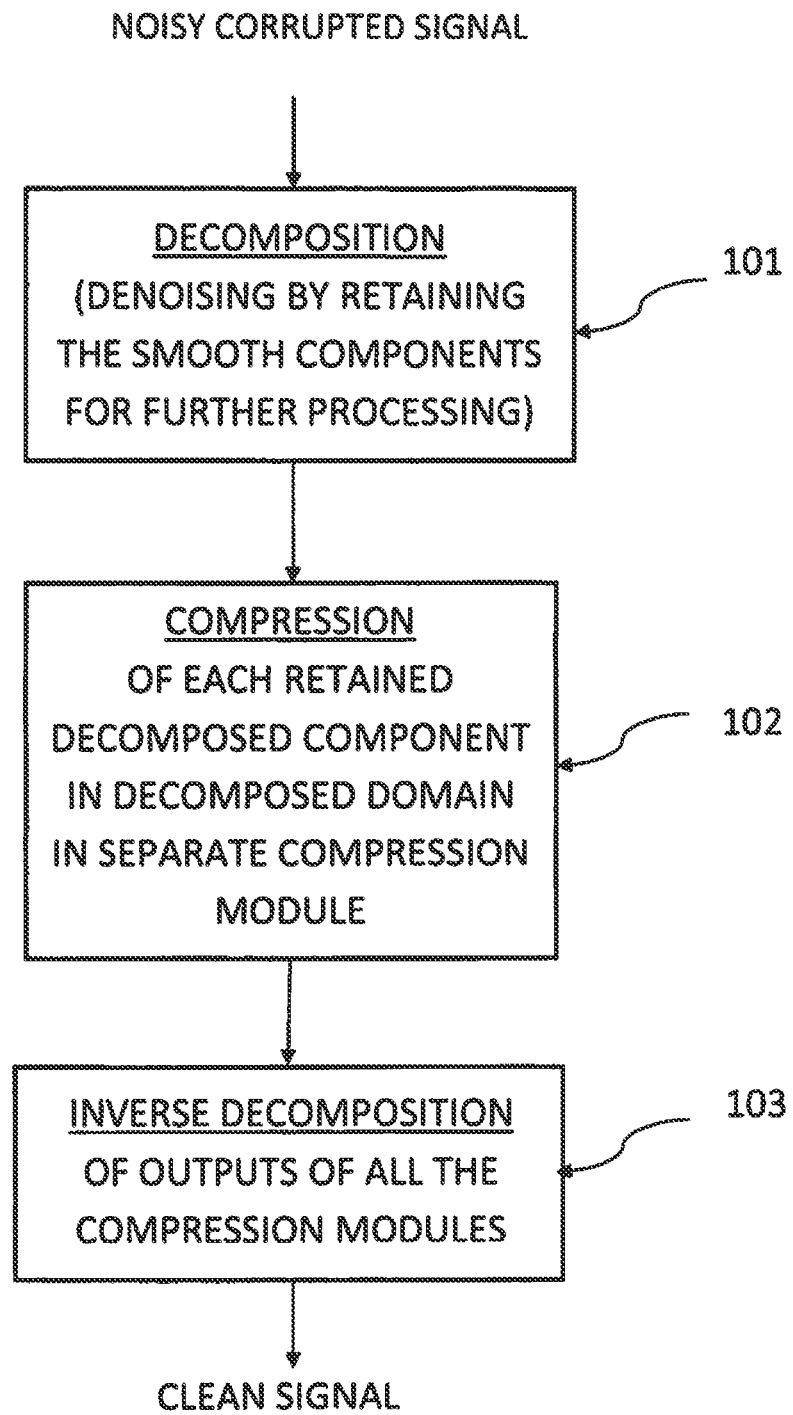
FIGS. 1A, B are a simple flowchart and simple functional block diagram, respectively, of a signal processing method and system of the present invention for extracting signals from noisy data.

The signal extraction process of the present invention can be summarized by the following sequence of operations: (a) decomposition of the signal into multiple scales which reveal different levels of details, (b) compression of signal components, using separate compression modules for signal extraction working in the decomposed domain for each retained decomposed component, and (c) applying an inverse decomposition to the outputs of all the compression modules to return a clean signal in the time domain. This sequence of operations is shown in FIG. 1A. Incoming noisy data is first transformed and segmented by decomposition at step 101 into decomposed components of different scales. A certain amount of noise may be rejected by keeping/retaining only the smoothest component or certain smooth components to be passed on for further processing. It is appreciated that other conventional denoising techniques may also be employed. At step 102 each of the retained components is then compressed by inputting into a corresponding compression module for the purpose of extracting the relevant signals in the decomposed domain. All the results from the compression modules are then inverted through an inverse decomposition at step 103 back into a clean signal in the time domain. Though not shown in the figures, background or other long-scale-length variations may be optionally removed (removal of baseline) through, for example, spline-fitting.

Figure 1B:
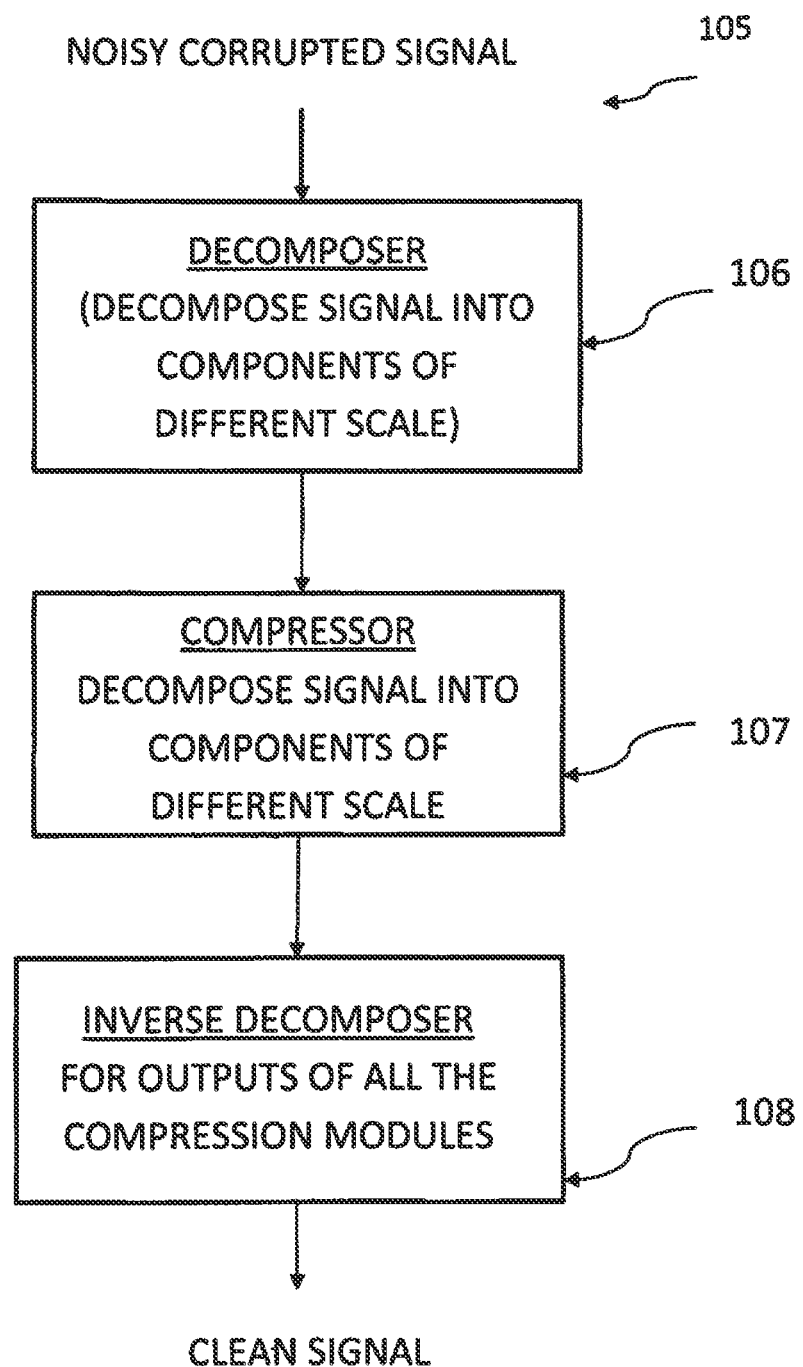

In the corresponding system 105, shown in FIG. 1B, the noisy corrupted signal is first input into a decomposer 106 in which the noisy signal is decomposed into components of different scale. Selected (retained) decomposed components are then input into compressor 107. Compressor 107 includes a separate compression module for each retained decomposed component. Compressor 107 may thus have as few as one compression module but typically will have multiple, depending on the number of levels or scales selected. Compressor 107 operates in the compressed domain. The outputs of compressor 107 are input into inverse decomposer 108 which provides a cleaned up time domain signal.

With respect to step 101 and decomposer 106, decomposition is preferably performed using discrete wavelet transform. The discrete wavelet transform ("DWT") provides sufficient information for both analysis and reconstruction of the original signal with significant reduction in computations. DWT is a form of multiresolution analysis, which provides an effective balance between the resolution requirement and the computational loading. Instead of using some thresholding techniques to eliminate noise as is often done for denoising for either wavelet or Fourier transforms, the inherent decimation procedure of DWT is used to eliminate noise in the present invention as follows. A simple discrete wavelet transform produces two sets of data from an original one: a "smooth" component part and a "rough" component part. The "smooth" part of the decomposition is a sort of local average, while the "rough" part contains the fine details. The "smooth" part of a decomposition level may be further decomposed to produce an additional higher level set of "smooth" and "rough" parts corresponding to a greater length scale. This operation can be further repeated to produce a series of decomposed wavelet components corresponding to different length scales, and comprising a highest order smooth component, and one or more rough components associated with each decomposition level. It is notable that the highest order smooth component corresponds to the $n^{th}$ decomposition level, where n is the total number of decomposition levels. Repeating each decomposition step also results in decimation by a factor of 2 (using only every second point). The "smooth" and "rough" parts thus have half of the points of the original, adding up to the original number of points, to within edge effects. This means that the decomposition has enough information in it to reconstruct the original, which is also true for repeated decomposition steps.

Another preferable technique for decomposition is a multiresolution pyramid scheme using multiple neural networks with the simplest scheme based on linear neural networks performing successive averaging to obtain higher and smoother scales as one moves up the pyramid to lower and lower resolutions. One can retain the neural networks from the upper portion of the pyramid to eliminate certain noise.

Figure 2:
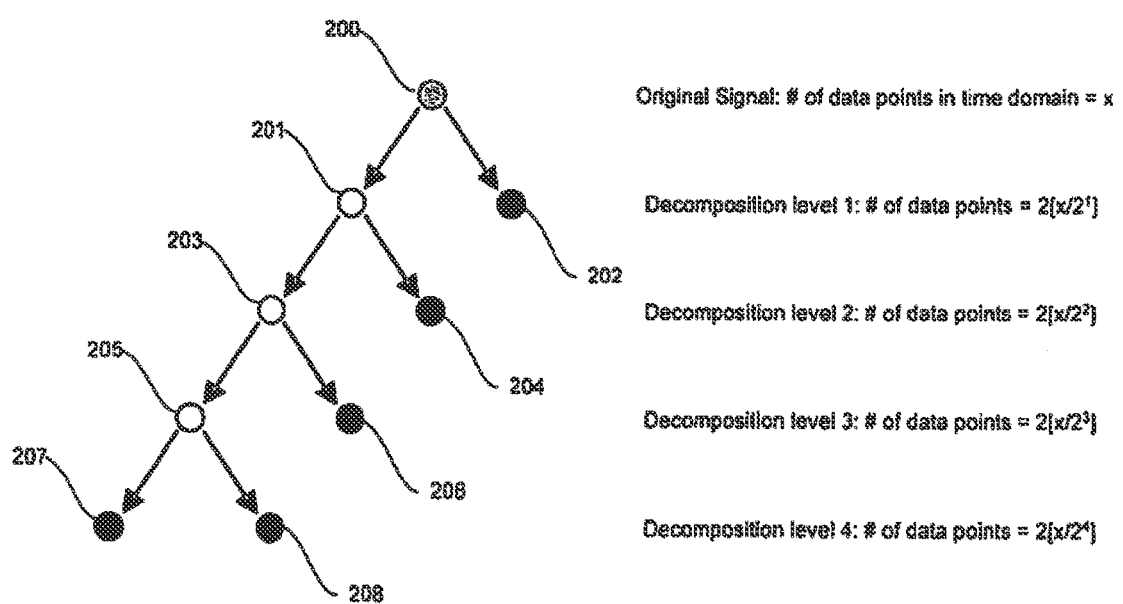
FIG. 2 is an exemplary four-level discrete wavelet decomposition of data.

An illustrative example of a four-level decomposition is shown in FIG. 2. The original signal is indicated at 200, which is decomposed at a first level to produce a smooth component 201 and a rough component 202. At a second decomposition level, the smooth component 201 is further decomposed to produce a smooth component 203 and a rough component 204. At a third decomposition level, the smooth component 203 is further decomposed to produce a smooth component 205 and a rough component 206. And finally at a fourth decomposition level, the smooth component 205 is further decomposed to produce a smooth component 207 and a rough component 208. For this four level decomposition, the smoothest scale (i.e. $4^{th}$ level smooth component 207) has the number of points reduced by a factor $2^4$ or 16. A four level decomposition results in $[x/(2^4)+x/(2^4)+x/(2^3)+x/(2^2)+x/(2^1)]$ or x number of data points in the wavelet domain. As a result, the discrete wavelet transform retains the same number of the data points as in the time domain.

For the higher decomposition levels, accompanying such data point reduction is the elimination of certain high frequency noise. Since the signals are mostly embedded in the higher decomposition levels, the lower decomposition levels can be ignored with little or no loss. In other words, noise is effectively reduced by retaining only the highest order decomposed components, beginning with the smoothest, i.e. as an example the $4^{th}$ level smooth component 207 in FIG. 2, since most of the noise is in the rough components. While not all possible combinations of mother wavelet types and different numbers of decomposition levels for each wavelet setting have been explored, results from experiments conducted by Applicant suggest that the smoothest level of such decomposition essentially captures most of the clean target information. The wavelets are scaled and translated copies (known as "daughter wavelets") of a finite-length oscillating waveform (known as the "mother wavelet"). For example, a four-level Daubechies-2 decomposition is found to be very effective in using the smoothest wavelet component, which in general contains most of the real signal for signal recovery, and yields a 16-fold reduction in the amount of the data for the neural network to learn. And there are only four points to describe the mother wavelet, so it is computationally much less demanding than other higher order choices.

There are some families of wavelet that are well-adapted for working with discrete data, notably the orthogonal Daubechies, and the Coifman families and some biorthogonal ones. Their (bi)orthogonality makes reconstruction very simple. It is appreciated that orthogonality is a property which greatly simplifies the reconstruction part of a transform. Orthonormal bases may not be available for every type of application. In such cases, a generalized version using biorthogonal bases can often be used. In contrast, it is notable that mother wavelets commonly used in continuous wavelet transform (CWT) analysis often lack convenient reconstruction algorithms in the case of discrete data points, which is what one has to work with in the "real world", as opposed to abstract mathematics.

In addition to the highest order smoothest component, additional rough components, beginning with the highest order, may also be retained for use as inputs into corresponding compression modules. If every level is kept, then such decomposition purely acts as a mechanism to assist the subsequent compression modules by partitioning the data to allow and facilitate the use of multiple compression modules and that by itself does not serve any purpose for denoising.

Figure 3:
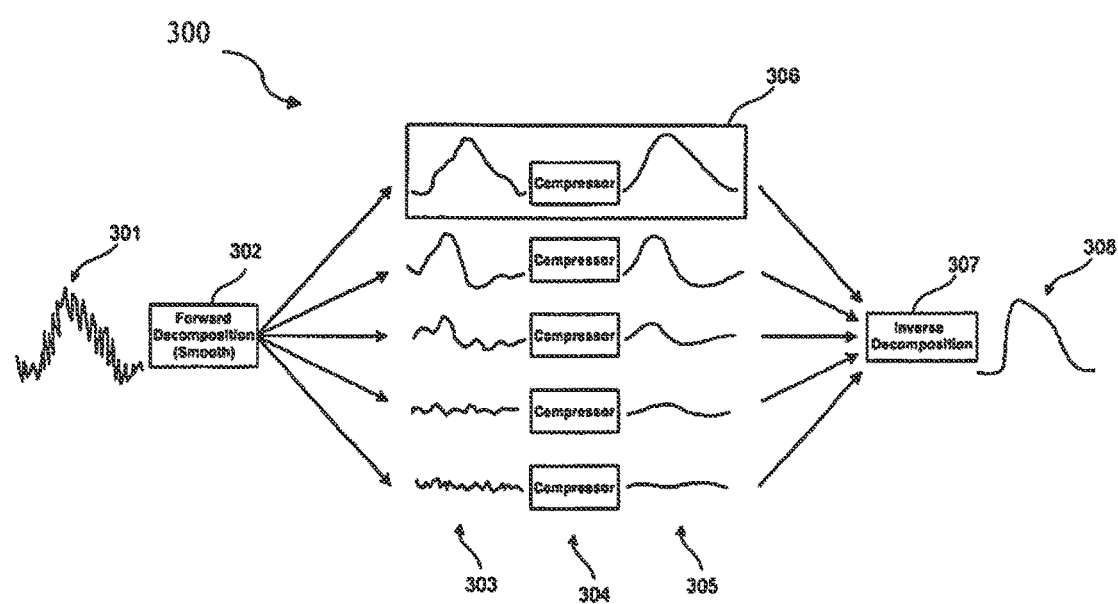
FIG. 3 is a schematic view graphically depicting the procedural flow of the signal preprocessing operation of FIGS. 1A, B.

FIG. 3 shows a system 300 for the decomposition of a noisy signal into multiple components, the compression of those decomposed components, and the inverse decomposition of the compressed components to produce a cleaned up signal. System 300 of FIG. 3 is a more detailed view of system 105 of FIG. 1B. A noisy signal 301 is passed through a forward decompressor 302 where the decomposition takes place. Decomposed components are produced as indicated at 303, with the top layer shown as the smoothest component. Each of the decomposed signals is then passed into a corresponding compression module, indicated at 304 (which collectively correspond to compressor 107 of FIG. 1B), to produce corresponding outputs 305 in the decomposed domain. The outputs are then combined at an inverse decomposer 307 where the signal is returned to the time domain as signal 308. In a preferred embodiment, decomposer 302 is a wavelet transformer and inverse decomposer 307 is an inverse wavelet transformer, particularly discrete wavelet transformers, and compressors 304 are auto-associative neural networks.

The top level which is shown enclosed in a box 306 indicates the use of only the smoothest component as input into a corresponding compression module 304. In the alternative, additional rough wavelet components may be used in conjunction with additional compression modules 304. It is appreciated that while use of just smoothest level decomposition may work for oversampled situations (with a high data rate), additional rough wavelet components may be retained and used depending on the data rate. For lower data rates or targeted data that fluctuates more substantially, additional rough components may be required, with additional corresponding compression modules to handle such inputs, because just one level of decomposition may not be able to capture the intended signals. In this regard, the present invention also enables the flexibility to choose the number of levels to decompose the incoming data stream, as well as to choose the number of components to retain for further processing. This progressive technique has the advantage of selectively trading off computation time and complexity versus signal extraction accuracy, and gives a user a greater handle on the course of action to be taken. For example, if one needs to add the next-smoothest level into the process, then the amount of computation will approximately double—that next level is the same length as the smoothest one.

As shown by the example of FIG. 2, the computational requirements for wavelet decomposition are not linear with the added levels but geometric, increasing as powers of 2. For example, the computational load for adding a second rough component 206 (i.e. a third retained wavelet component in addition to the $4^{th}$ order smooth component 207, and the $4^{th}$ order rough component 208) level will again double because the third retained wavelet component has a computational load equal to the first and second retained components (207, 208) combined. Such progressive signal extraction procedure allows a user to first find out whether the signal is of interest or not. If a signal is determined to be interesting, then additional processing using information from additional scales can enhance the outcome at the expense of processing power and time.

The down sampling of the incoming signal by decomposition processing is also advantageous to the compression modules, because at the highest order decomposition level for a 4-level decomposition, a reduction of the number of data points by a factor of 16 will actually reduce the computer load for the compression module by a factor of 16, because the smoother sub-sampled data is more noise free, meaning that will take less time to squeeze out noise in addition to the effect of the dataset size being smaller. For the next order decomposition above the smoothest, again one also has a factor of 8 advantage in data reduction, but this scale is less smooth. And the next order decomposed component will have a reduction of data points by a factor of $2^3$ or 8.

In this manner, decomposition, such as by the use of discrete wavelet transform (DWT), serves three different purposes. First, it provides a means to segment the data in a way that enables time-saving progressive processing. Second, since signals most often occur within the smoother scales, such decomposition enables automatic data reduction if one chooses to ignore the less smooth scale. And third, the smoothness of the lower scales allows the compression module to perform better in those component domains by rejecting a certain amount of noise before the component signal is then passed onto the compression module for the purpose of extracting the relevant signals. Cleaner signals bring out the features more clearly and thus are easier for the compression module to process. In other words, the decomposition transform provides a way to "transfigure" the data into a domain that favors compression processing.

With respect to step 102 and compressor 107, each of the retained components is then processed by its own corresponding compression module 304. An important point is that the compression module processing here does not process data in the time domain but within the decomposed domain to take advantage of both smoothness of the signals and the data reduction in the smoother scales. The compression modules 304 of compressor 107 are inserted between the decomposer 106 and inverse decomposer 108, i.e. between the decomposition at step 101 and the inverse decomposition at step 103, so they work in the decomposed domain instead. Such a combination of decomposition, compression, and inverse decomposition is uniquely designed to tackle the problem with no information regarding what the pure signals would look like.

Secondly, by using or allowing more than one compression module, separate compression modules may handle separate decomposed signals representing different scales, and thereby avoid overtaxing any one of the compression modules. While a compression module might uncover almost any signal features, by using simpler compression modules enabled by the division of signal extraction over multiple compression modules working at different scales, this greatly improves system efficiency. This is because the degrees of freedom are fewer. This allows a progressive system that enables selective tradeoff between computational complexity and accuracy. It is appreciated that if one chooses to use an adaptive compression technique such as one based on an auto-associative neural network, because of the adaptiveness, the decomposition procedure, such as in the case of wavelet preprocessing, need not be precisely tuned for absolute optimal denoising. The two signal processing systems (signal decomposition and compression module) probably overlap and thus yield a more flexible or "forgiving" signal processing.

The function of each of the compression modules is to extract the relevant signal in the decomposed domain from a corresponding decomposed component. Unlike most equipment such as gas chromatographs or mass spectrometers, which are governed by laws of physics and thus one would be able to derive certain well defined theoretical ideal signals from first principle, systems such as biological systems are far more complicated and, as a result, for these systems one cannot at this point derive the behavioral features from first principle and thus one could not have ideal clean target signals for supervised training based on recognizing known clean signals from the corrupted ones. For example, no one has any idea of the behavioral features of clean brainwave signals. Without clean signals, supervising learning becomes impossible since there are no targets to learn from. Thus, the compression systems, which are embedded inside the decomposition domain, need to function without any idea what the clean signals should look like to uncover the real signals from the corrupted ones. As a result, unsupervised learning or self supervising learning to uncover real features is needed.

A compression system is defined here as one that "squeezes" out unnecessary bits and at the same time produces output signals that resemble the input ones. The outcome in satisfying these two requirements is noise being dropped since typically noise fluctuates much faster than signals and this is especially true for brainwaves since brainwave signals tend to be slow. One form of implementation of such a compression system is a self-supervised auto-associative neural network. Another form is vector quantization. But the current invention is not limited to just these two compression techniques.

An auto-associative neural network is a neural network with an equal number of input and output neurons in the input and the output layers. However, structurally the number of neurons in the hidden layer is limited and less than the number of the input or output neurons. In the case of a supervised training neural network, one has input and output pairs with the outputs being the target clean signals and the inputs being the noisy signals. In auto-associative neural networks, there are no such input-output pairs. Training is self-supervised and it is done by "creating" an output behavior that closely matches the noisy input behavior by adjusting the synaptic weights between the input and output layers. But because the hidden layer has a limited number of neurons, not all the information from the input layer can pass onto the output layer. Parts of the corrupted inputs will be dropped because of the constraints imposed by the smaller number of neurons in the hidden layer. Since the training process is aimed at closely matching the outputs to the inputs, the outcome is that noise is being discarded by such processing because noise is rapidly changing from one set of inputs to the next, leading to eliminating the noise in favor of passing only the relatively stable signal information.

Another way of looking at this is that real information tends to be well-behaved and thus its representation takes fewer bits whereas noise is random signals and thus requires more bits. Thus dropping noise will be most efficient to reduce the total bit representation of the corrupted signals when one tries to do a compression. In the case of an auto-associative neural network, the limited "passage" provided by the smaller number of neurons in the hidden layer squeezes down the bit representation. In other words, the hidden layer "squeezes out" the noise to pass along the real relevant signals to achieve maximum closeness between the inputs and outputs. However, if the number of neurons in the hidden layer is over constrained then part of the real signals would also be dropped and thus the network will not only reject noise but will also lose signals. Finding the appropriate number of hidden neurons in most cases is an art or by trial and error. Training of neural networks has been done by a variety of means, but the configuration described here and related configurations are most commonly trained with backpropagation or "backprop" for short. It starts with a measure of the neural network's error based on typically randomly selected weights connecting the neurons between the layers, usually the sum of the squares of the differences between the desired output values and those calculated with the neural network, the same as would be done in least-squares fitting. Some training algorithms can start with this error directly, but more efficient algorithms become available when one finds the gradient of the error with respect to the weights. This gradient is found with the help of the chain rule, which goes backwards in the neural-network architecture until it finds the weights, thus the name "backpropagation". Preferably a projection neural network is used in the present invention. A projection neural network projects the original input vectors into a space with one higher dimension before feeding the projected vectors into a single-hidden-layer feed-forward backpropagation neural network. And a modified Logicon projection system is preferably used for this processing. When considering the computational load when a system is deployed in the field, certain decomposition systems such as full-scale wavelet transforms are computationally demanding. While training a neural network may be demanding, deploying neural networks is computationally simple because neural network processing is highly asymmetrical. In deployment, a neural network typically does not have to learn, which is a more time-consuming iterative process, and thus it can execute its computations very fast. It is appreciated that all neural networks can work in a totally parallel fashion to increase the processing speed. This combination minimizes the demand of CPU time or hardware when one deploys the algorithm out in the field.

At step 103 of FIG. 1, all the output results from the compression modules are then inverted and reassembled through an inverse decomposition back into a clean signal in the time domain. In this manner, a clean signal is produced at the end.

The method and system of the present invention should be generally applicable to a variety of noisy signals with no known clean signal and thus not amenable to traditional supervised neural network training. The current method works on any one-dimensional array, so spectra such as EEG and MEG signals are treatable. Extensions to two-dimensional data (e.g., spectra versus time) are possible. Also, the technique of the present invention is extendable to 2D data (e.g. images) or even higher dimensions. It is expected that adding extra dimensions will actually help the compression modules perform even better because of the additional constraints or hints provided from the added dimension(s) of data. The computation load for the compression modules will go up with the dimension and the number of data points in the decomposed domain. However, here also, the number of data points in the decomposed domain will also be reduced by the same power due to the use of decimation. For example, for N data points in a 1-D signal, a four level decimated wavelet transform will have N/16 points for the compression module to process if only the smoothest level is included. Now if there are N data points in each of the dimensions in a 2-D image, then the number of data points to be processed in the compression module will be $(N/16)^2$ or $N^2/256$ if again only the smoothest level is included. So the use of decimation through wavelet preprocessing or similar decimated preprocessing really helps to reduce the computational load.

Figure 4:
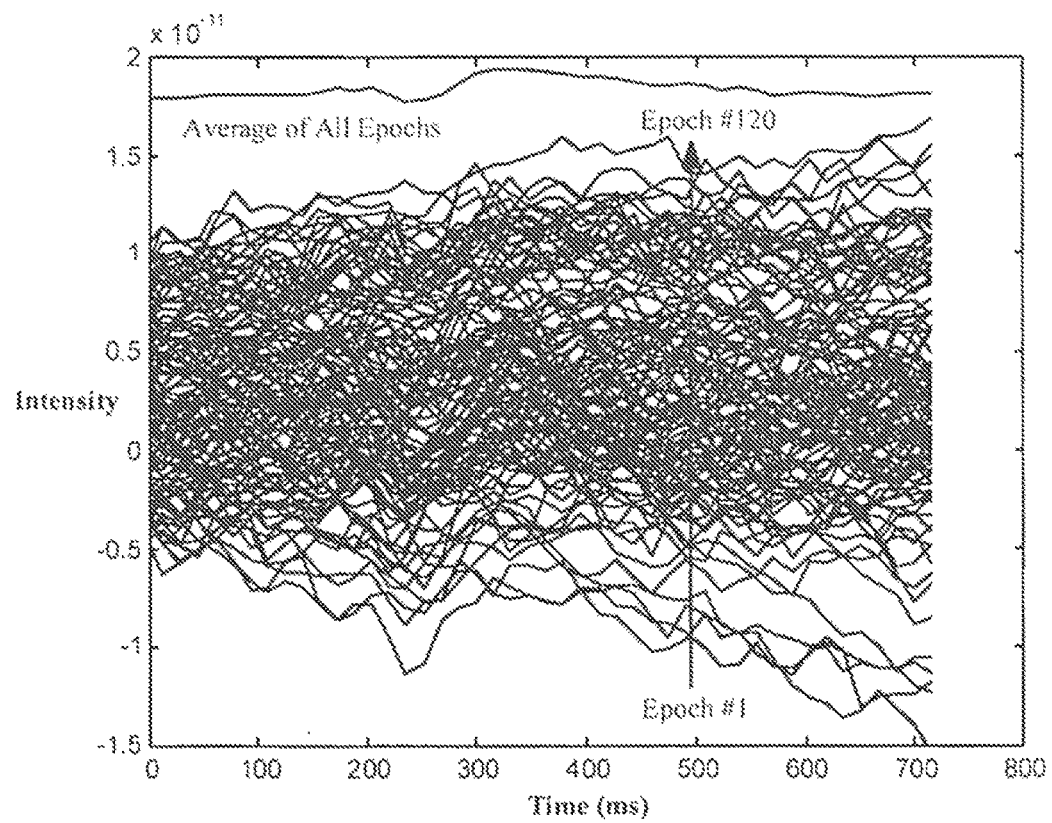
FIG. 4 displays the noisy raw MEG signals from 120 repeated measurements at the same location.
Figure 5:
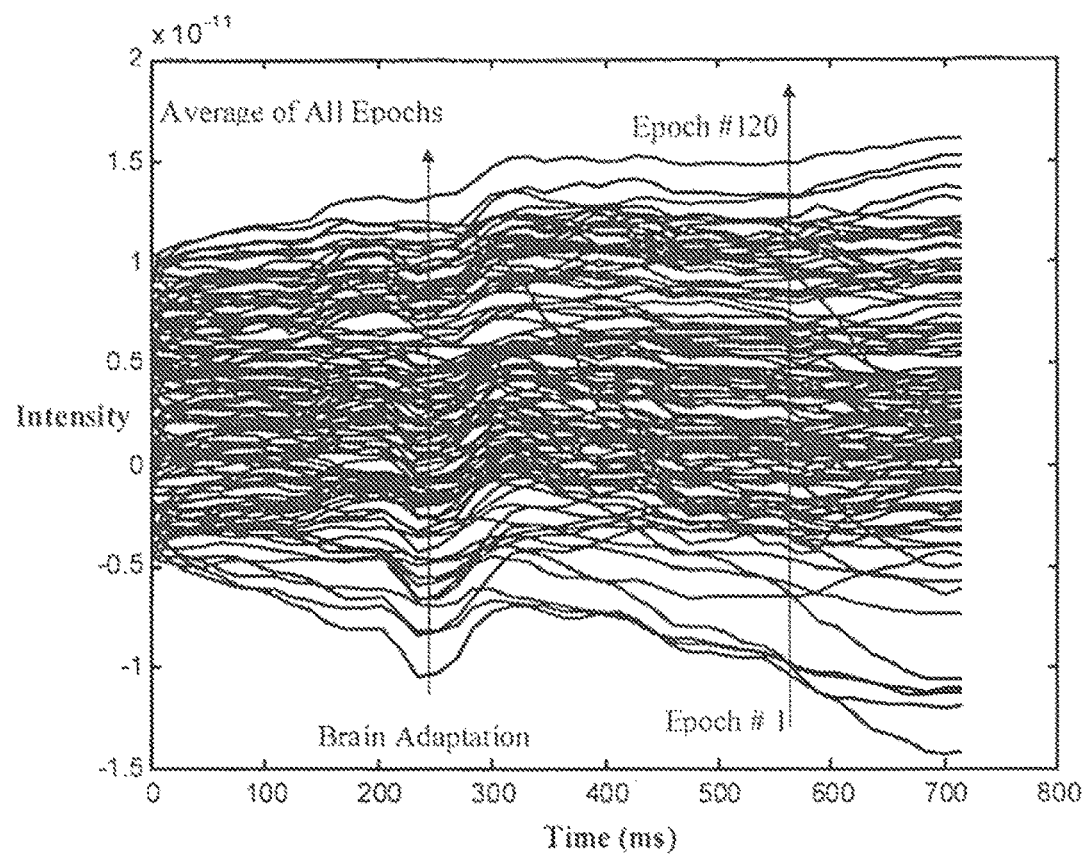
FIG. 5 displays the cleaned up MEG signals from the same 120 repeated measurements from FIG. 4.
Figure 6:
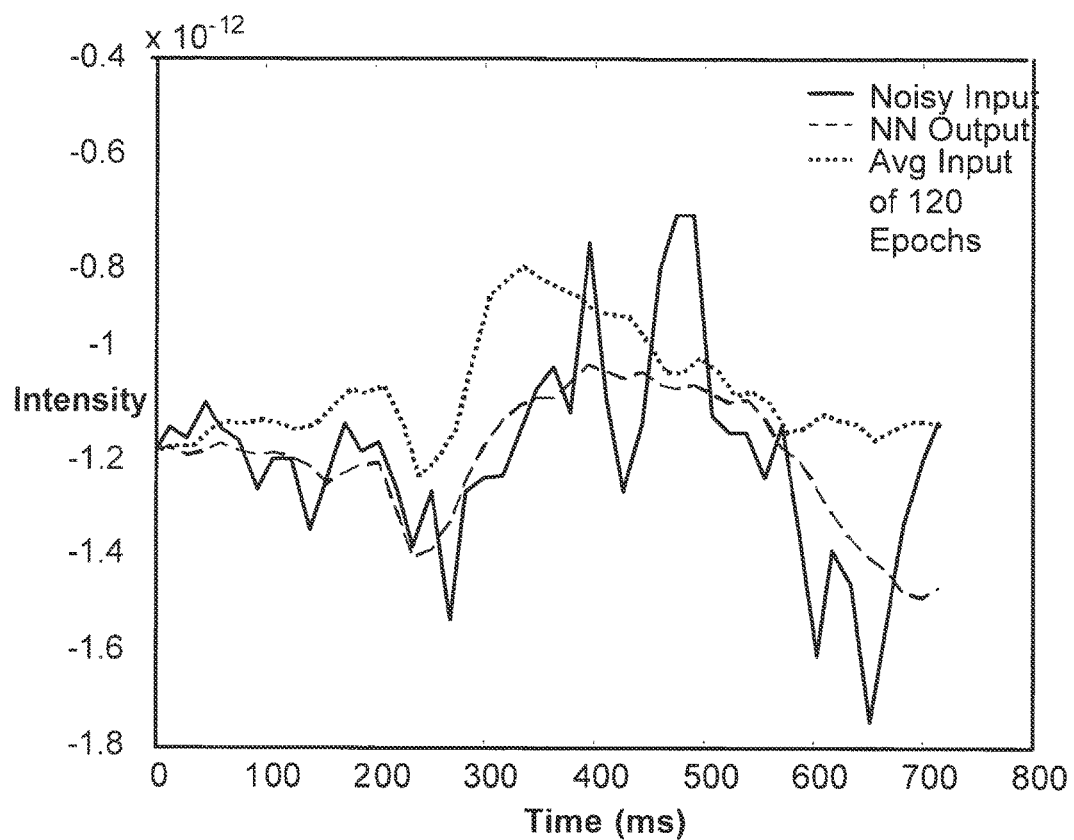
FIG. 6 is a graph showing one of the raw noisy MEG signals, the corresponding cleaned up MEG signal, and the signal averaging results from the 120 noisy raw MEG signals.

Using the technique of the present invention, it is possible to reliably extract, for example, brain wave signals from EEG or MEG. This method has been demonstrated to clean up certain brainwave signals. The MEG signals were collected when the subject listened to the same sound repeatedly from a tuning fork. The time sequence from the MEG signal is from before the sound is generated through the generation of the sound to after the sound died off. The same sounds were generated 120 times creating 120 MEG signals as a function of time. FIG. 4 shows the 120 raw noisy MEG signals as a function of time measured from the same location of the brain of the subject. FIG. 5 shows the same 120 signals processed by a combination of discrete wavelet transform and auto-associative neural network. As can be seen, much of the noise dropped out from the raw noisy signals. FIG. 6 shows a comparison between one raw signal and its corresponding cleaned up signal. The traditional approach to denoise MEG signals is based on signal averaging. Such an average from the 120 raw signals is also shown in FIG. 6. However, using such traditional processing would also imply loss of time resolution, a very undesirable feature since what sets EEG and MEG apart from other brain information extraction modalities such as PET and fMRI scans are that both EEG and MEG are real time whereas PET and fMRI have time resolution on the order of minutes. As can be seen, the processed signal is a much better representation of the real noisy signal than the result from the signal averaging technique because the peak of the raw signal and that from the averaging signals are mis-aligned, indicating the inadequacy of the averaging approach to represent an instance of the signal. As a result, traditional processing not only loses time resolution but it will also mis-represent the signals.

Figure 7:
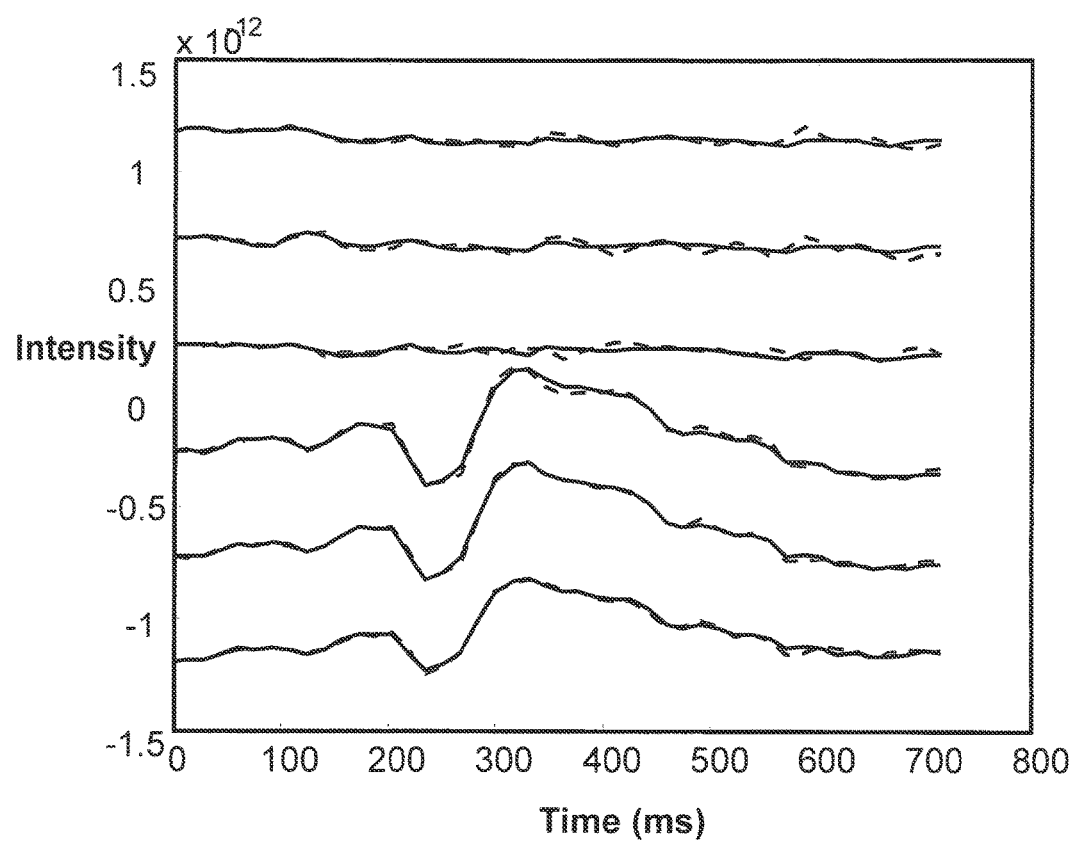
FIG. 7 is a graph comparing averaging out of the raw signals (in dotted line) to averaging out of the cleaned up MEG signals (in solid line). The 6 sets of curves are displaced vertically to show the results from 6 sensors at 6 different sensing locations on the head.

But how does one know that the present signal processing invention does extract the actual signal without creating any artifacts and without dropping any real signals. FIG. 7 shows signal averaging of the 120 raw signals together with the signal averaging of the 120 processed signals based on this invention measured from six different locations on the brain. Three of the brain locations responded to the sound stimulation and the other three did not. If artifacts were introduced, then the average processed signals and the average raw signals are unlikely to completely cancel out. FIG. 7 thus suggests that no artifacts have been introduced by the invention since the two curves almost lie on top of each other. Similarly, if some portion of the real signals were dropped, then again it is unlikely the dropped signals cancel out, resulting in the agreement between the two lines. So, in conclusion, the signals extracted are real. Furthermore, the extracted data in FIG. 5 show that the brain adapted to the repeated stimulation by progressively "ignoring" the repeated stimulation as evidenced by the decreasing responses of the signal represented by the valleys at ~240 ms. This phenomenon is in agreement with our biological understanding of the brain. The brain tunes out or blanks out repeated signals to prevent them from overloading the brain functions. (For survival, static signals do not pose a threat whereas any sudden movements can mean danger.) That is why deer would not be frightened by a nearby lion as long as the lion does not make a sudden move because the repeated sceneries of the nearby lion were tuned out. The application of the present invention to clean up brainwaves is illustrative of the broad range of possibilities resulting from this invention. The present invention may be implemented as software in an existing data processing/analyzing system, or embodied as firmware or hardware or the like, such as various processing chips (application-specific integrated circuit or ASIC, full-custom chip, digital signal processing or DSP chip, graphic processor chip or GPC) for real time processing, especially when handling the enormous amount of data that some 2-D or 3-D high-resolution sensors collect.

The invention also relates to a low-cost, non-drug, non-invasive, on-demand therapy braincap system which is pharmaceutically non-intrusive to the body. It relates to a technology based on recognizing abnormal brainwave signatures and intervenes at the earliest moment using magnetic and/or electric stimulations to reset the brainwaves back to normality. The feedback system is self regulatory and the treatment stops when the brainwaves return approximately to normal; as a result, therapy is only applied when needed; thus the intervention is delivered minimalistically.

The braincap equipment consists of an array of brainwave detection sensors, such as EEG microelectrodes, and an array of stimulation devices, such as microcoils that can generate magnetic fields up to Tesla level intensity or devices for electrical stimulation such as ear-point stimulations, to reset the brainwaves.

Figure 8A:
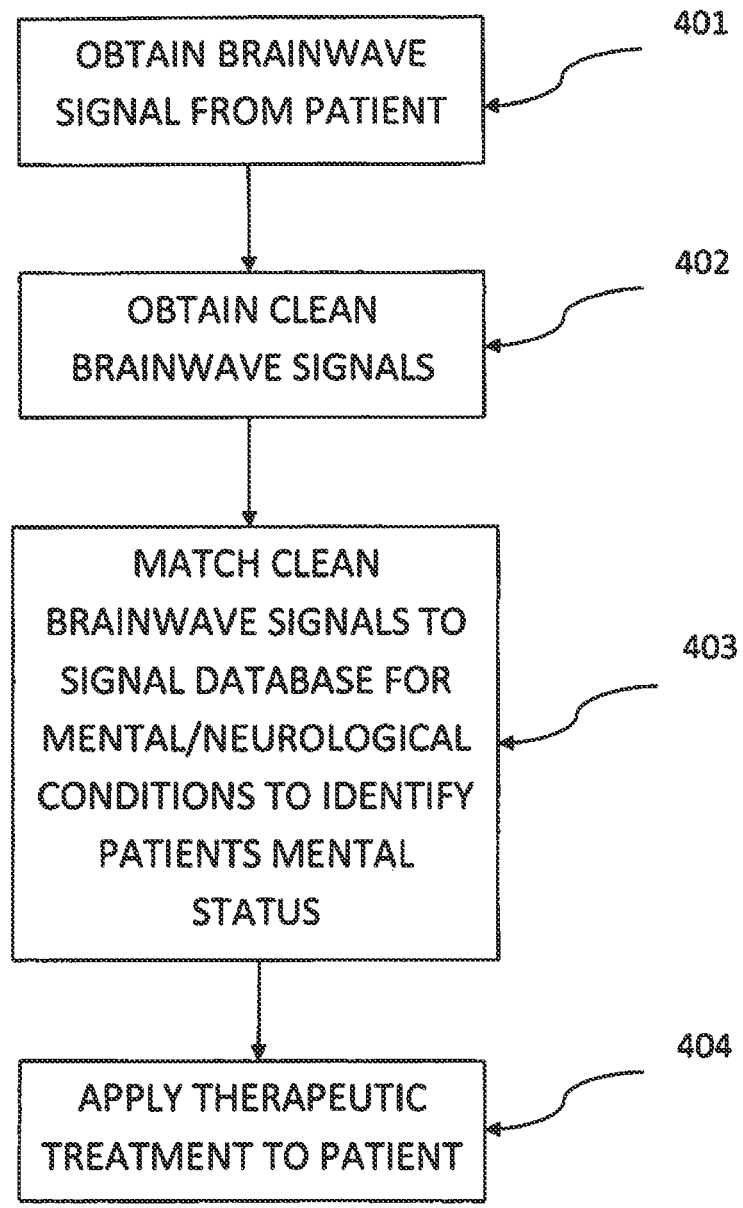
FIGS. 8A, B are a simple flowchart and a simple functional block diagram, respectively, of a treatment processing method and system of the present invention.
Figure 8B:
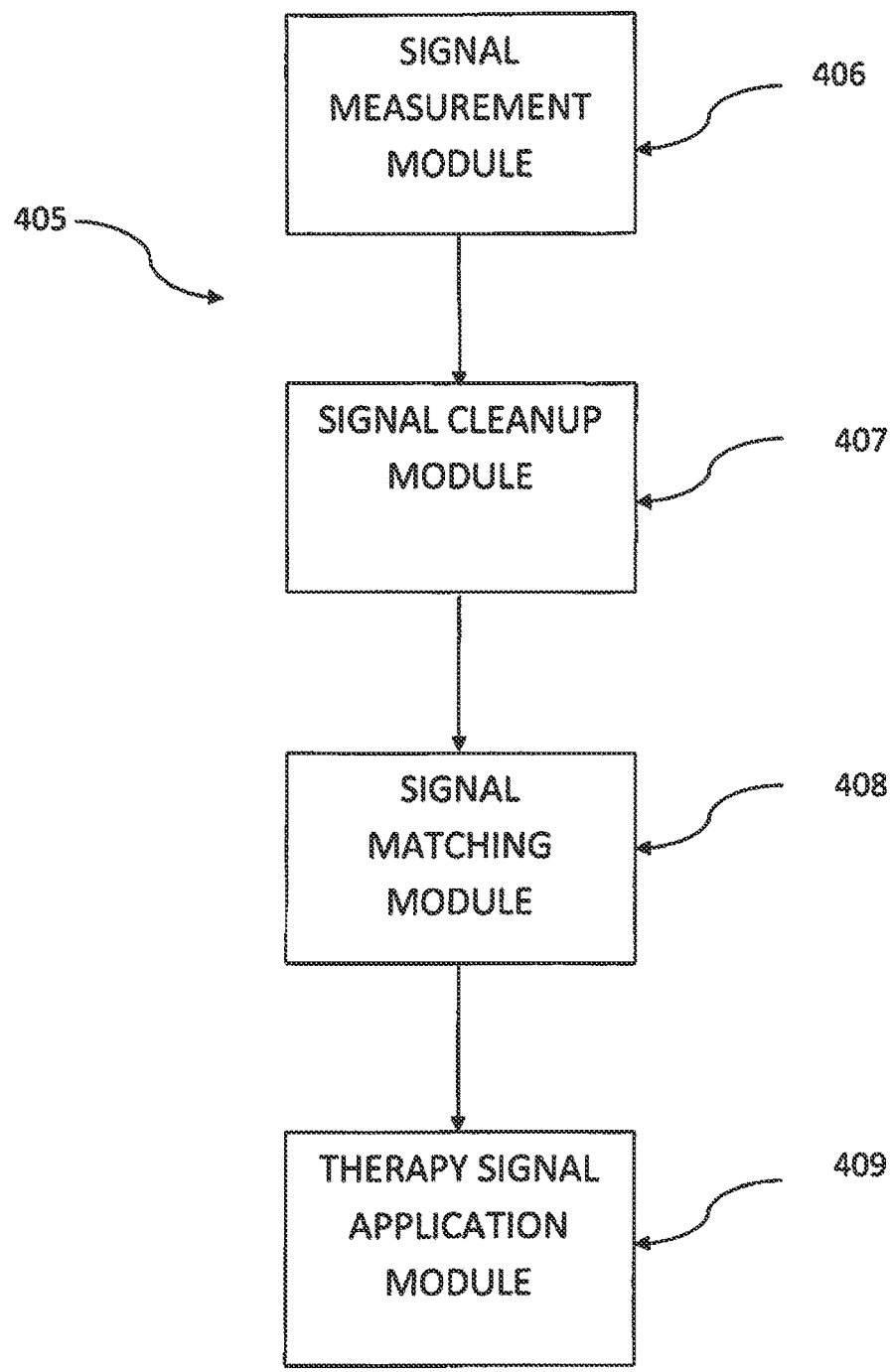

This invention includes a treatment system and method that leverage upon the clean brainwave signature obtained as described above to create on-demand, non-pharmaceutical, and non-invasive therapies for certain neurological/mental disorders and conditions such as PTSD, depression, epilepsy, Parkinson's disease, Alzheimer's disease, sleep disorder, attention deficit hyperactive disorder (ADHD), autism, pain management, schizophrenia, alcohol/drug craving, anxiety/panic disorders, and many others. This sequence of operations is shown in FIG. 8A. First, brainwave signals are obtained from a patient in step 401. The step after such measurement is signal processing to clean up the signals in step 402 as has been described previously. Afterwards, as shown in step 403, the cleaned up signal or the brainwave signature is compared or matched to the accumulated reference data/signatures of the various mental/neurological disorders in a computer or a signal processing unit to identify the patient's mental status. Or one can compare with stored brainwave patterns of the patient taken when he/she was not suffering from the disorder, such as when the patient does not have pain if treating the pain issue or tremor if treating a patient with Parkinson's disease. Upon identification or comparison, therapeutic treatment is applied in step 404. A corresponding system 405 for carrying out the method of FIG. 8A is shown in FIG. 8B and consists of four functional modules. Module 406 is the signal measurement module for obtaining brainwave signals from a patient, followed by module 407 for cleaning up the signal, as previously described. After module 407 comes the signal comparison or matching module 408, then the treatment application module 409. The matching in step 403 and module 408 need not be a perfect match but a statistically sufficient match to identify the condition.

Figure 9:
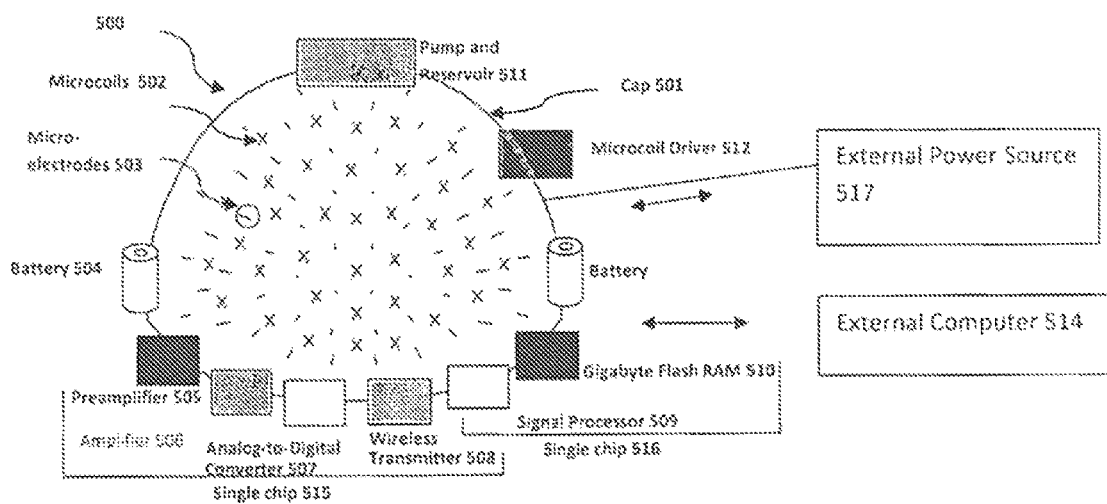
FIG. 9 is a schematic diagram showing a braincap populated with micro-electrodes for EEG measurements and micro-coils for repetitive magnetic transcranial stimulations.

FIG. 9 shows a brain cap 500 according to the invention. A plurality of microelectrodes 503 could be fabricated and inserted inside a cap 501 to form a dense array of EEG electrodes of an EEG monitoring system, together with a corresponding plurality of magnetic field generating microcoils 502 for repetitive transcranial magnetic stimulation or rTMS on the cap 501.

Microelectrodes can be fabricated using Micro-Electro-Mechanical Systems (MEMS) technology. The human scalp has a surface area of approximately 700 cm$^2$ and thus the surface area is large enough to accommodate both the electrodes and the coils because of their small dimensions. The number of microelectrodes and microcoils can vary widely, depending on application, from tens to over a thousand of each, with a few hundred to about four hundred being typical. Such headgear provides good topological mapping with unprecedented EEG spatial resolution for even the most demanding applications. Specific brain caps, such as one aimed at patients with depression or other ailments, would require far fewer electrodes and coils since it should not be necessary to monitor and stimulate every single region of the brain for any one disorder, as indicated by research done and reported by others. The invention is not restricted to EEG sensors; other type of brain sensors could be used in place of the EEG electrodes such as the superconducting quantum interference devices (SQUIDs) which generate MEG signals. Other appropriate sensors include infrared (IR) sensors, alkali vapor magnetometers, and other sensors that can sense the brain's activities.

Figure 14:
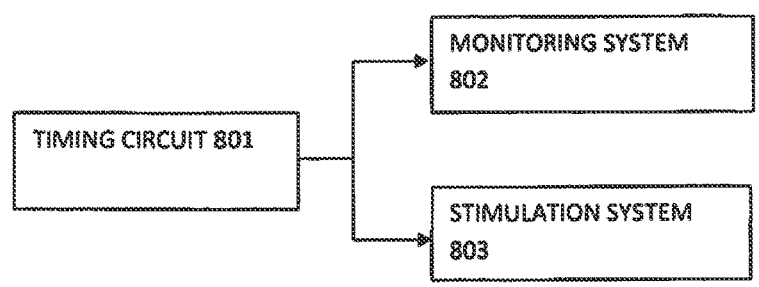
FIGS. 14A, B are a timing circuit and pulse sequence, respectively, for the microelectrodes and microcoils of a braincap of the invention.
Figure 14B:
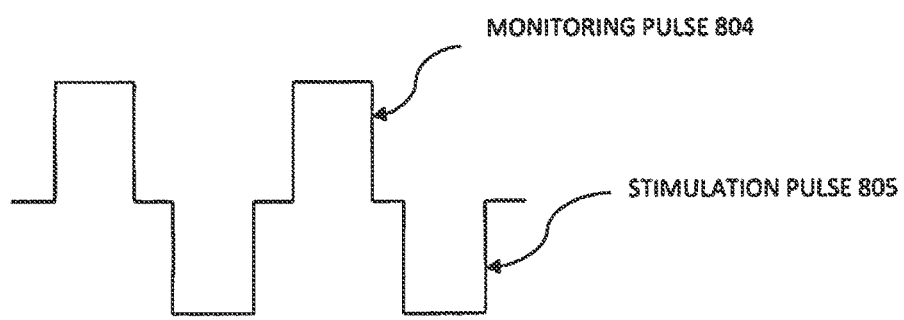

Various electronic components, e.g. a pre-amplifier 505, an amplifier 506, and an analog-to-digital converter (ADC) 507 for collecting the EEG signals from electrodes 503, are mounted on cap 501, extremely close to the signal sources to minimize noise for signal conditioning. However, the short but high power rTMS stimulation pulses could possibly damage these electronic circuits. Traditional EEG amplifiers could be blocked for a period of time of seconds to minutes due to saturation, and some amplifiers can even be damaged by the short but strong TMS energy bursts. As a result, the electronic circuits in this invention will be shielded properly. FIG. 14A shows another approach using a timing circuit 801 which switches between the brain activity monitoring system 802, such as EEG, and the stimulation system 803, such as rTMS. Timing circuit 801 provides a sequence of monitoring pulses 804 and stimulation pulses 805 that are stacked and do not overlap as shown in FIG. 14B. Yet another solution is for the amplifier to have a low slew rate so that it does not respond to the higher slew rate rTMS pulses. The collected signals can then be wirelessly transmitted using a low power transmitter 508 to a nearby computer 514 for further signal processing or such processing can be handled onboard with a signal processor 509 and its associated flash memory 510. The pre-amplifier 505, the amplifier 506, the ADC 507, and the wireless transmitter 508 can be integrated into a single chip 515 to reduce weight and cost as well as to improve efficiency, or they may be individual chips. Similarly, the signal processor 509 and the memory 510 can also be integrated into a single chip 516. A microcoil driver 512, formed of one or more chips, is also mounted on cap 501 to drive the currents through the microcoils 502 for magnetic stimulation. Powering of these chips can be done with batteries 504 mounted on the cap 501 so the entire system can be mobile and/or by wire connection to an external power source 517. Alternatively, using RF coupling, some limited power can be "beamed" from external power source 517 as shown with the double arrow in FIG. 9 to the electronics on the cap to power certain operations without the presence of the batteries. This is possibly a good solution for nighttime operation where the "beaming" unit is right by the bedside.

Figure 10A:
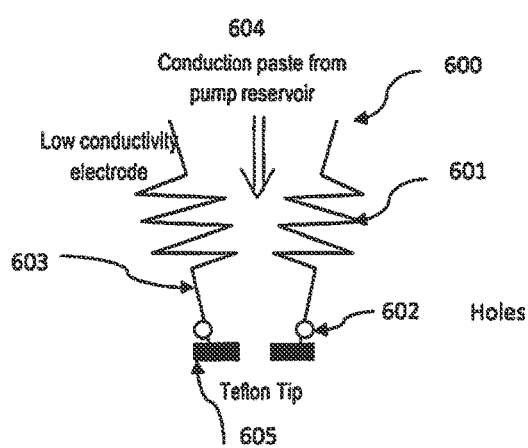
FIGS. 10A, B show a microelectrode, and a cross-section of its tip, respectively, for collecting EEG signal from the scalp of the head.
Figure 10B:
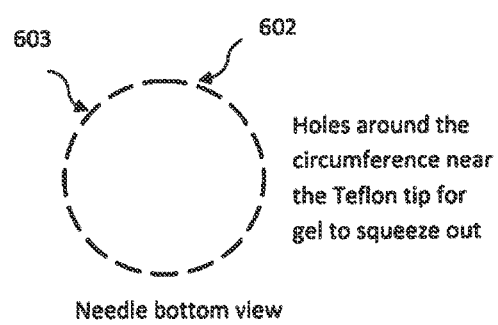

FIGS. 10A, B show an EEG microelectrode 600 that can be used in the cap. The electrode 600 is made of hollow microtubing 603 on the order of 1-3 millimeters in diameter with electrically conductive fluid 604 inside for securing better signals. A portion of tubing 603 near the tip is formed into bellows 601. This microelectrode is larger than a typical needle electrode which is 27-28 gauge or about 0.32-0.4 millimeters in diameter. The impedance of such a needle electrode is preferably between 100 and 10,000 ohms. When correctly inserted, impedance should measure between 5000 to 8000 ohms and the inter-electrode impedance differences should be within 2000 ohms. Such inter-electrode impedance matching is often difficult to achieve with surface disk electrode applications. The high impedances of needle electrodes, including the one described here, affects the signal-to-noise ratios, and thus cleaning up signals as described herein is paramount for the best final signal outcomes. The bellowed tip allows fine adjustment and pressure contact to the scalp of the patient to ensure good contact. The Teflon coated tip 605 of the electrode provides gentle contact to the scalp. Near the bottom of the electrode, additional holes 602 are fabricated around the tubing along the circumference near the Teflon tip. More than one row of holes could be used. After a patient puts on the cap, the conducting paste or gel or even saline fluid is forced into the electrodes by a micro-pump 511 mounted on the cap (shown in FIG. 9), to further assure good electrical contact. Such fluid will flow out of the holes around the tip and thus the actual contact area is not determined by the diameter of the tip but determined by the amount of gel/paste flowing out of the holes creating additional larger contact areas for the scalp. This invention is not limited to the microelectrode of FIGS. 10A, B. In place of this microelectrode other types of sensors such as near infrared sensors, traditional disc EEG electrodes, sub-dermal EEG needles, superconducting quantum interference devices, and alkali vapor magnetometers can be used.

TMS, besides impacting the electronics, can also induce eddy currents in traditional metal EEG electrodes, creating heat, and thus can be a risk for damaging the tissue under the electrode. The use of many lower power microcoils behaving somewhat like a phase array arrangement instead of a single high power coil should minimize the impact on heating up the electrodes and damaging the electronic circuits. Microelectrodes have much smaller mass due to the greatly reduced dimensions compared with traditional disc electrodes, which have a diameter of 1 cm, and should also minimize the eddy current effect. Low thermal conductivity materials could be used for the fabrication of the electrodes. The Teflon tip acts as a heat barrier to prevent heat transfer and thus reduces heat damage to the skin. The conducting paste or gel chosen has the properties of good electrical conductivity but poor thermal conduction, and thus helps to minimize tissue damage. One such material is conductive polymeric epoxy since polymer materials have poor thermal conductivity. Another option is to use certain polymer nanocomposites as the conductive paste/gel.

After collecting and cleaning up the brainwave EEG signals, the next step is to identify the signature. Matching or comparing to the database to recognize the signatures corresponding to mental/neurological disorders can be done by various means. In all cases, brainwave signatures corresponding to various ailments as well as normal signatures are collected from patients and control subjects without any mental/neurological disorders. This data can be processed by different methods for identification of mental/neurological disorders. For example, one can train a neural network to distinguish a normal brainwave signature from the signature of patients with depression. In this particular case, supervised training could be used since one will have a target signature to learn from. If so, then the use of a Logicon projection network would be preferable. Furthermore, one can add more noise to the dataset to create a more robust recognition process. Such a neural network could have multiple outputs, with each output corresponding to one disorder. Or one can have a number of dedicated neural networks, with each neural network only having one single output; thus one neural network will correspond to one disorder. These approaches would identify multiple concurrent disorders. For example, a patient with PTSD could also have concomitant depression. Another totally different type of neural network that could be used is the Kohonen self-organizing map (SOM). This is an unsupervised approach as opposed to the supervised approach mentioned above for supervised neural networks such as the Logicon projection neural networks. The data will be automatically sorted and classified by the SOM. Yet another approach is to use vector quantization. In that case, the n sensor responses will become the components of a vector with n elements. The patient's measured brainwave signature vector after denoising will then be compared to the centroid vectors corresponding to the various disorders. And yet another approach is based on traditional Bayesian statistical calculations. In this invention, all or some of these analysis methods are used to give a meta-analysis to increase the accuracy of the matching and thus improve diagnosis. These brainwave signature measurements not only could provide monitoring of the patient's neurological status but also can perform an initial diagnosis analysis along with the traditional diagnostic method using the Diagnostic and Statistical Manual of Mental Disorders V (DSM-V) manual. This is an important consideration since there are some questions regarding whether the current methodology based on DSM under-diagnoses or over-diagnoses certain neurological disorders, e.g. PTSD or bipolar disorder. For example, according to *Bipolar Depression, a Comprehensive Guide*, only 78% of bipolar disorders were diagnosed using the DSM manual. Missing about one quarter of the potential sufferers could be an important consideration. Also, it is conceivable that minor brainwave alternations would precede physical symptoms of neurological diseases such as slight tremors of fingers which could signify the beginning of Parkinson's Disease and thus the present invention could possibly provide earlier diagnosis than the traditional diagnostic approach, resulting in pre-emptive intervention and monitoring, resulting in improving the chance of recovery or containment of the ailments.

The present invention uses a dense array of miniaturized coils or microcoils, and more preferably cross-coupled microcoils. The fabrication of these coils could be done using Micro-Electro-Mechanical Systems (MEMS) based fabrication technology using conventional lithography or using the laser pantography direct write technology as described by U.S. Pat. No. 6,417,754 or conventional technologies.

Figure 11:
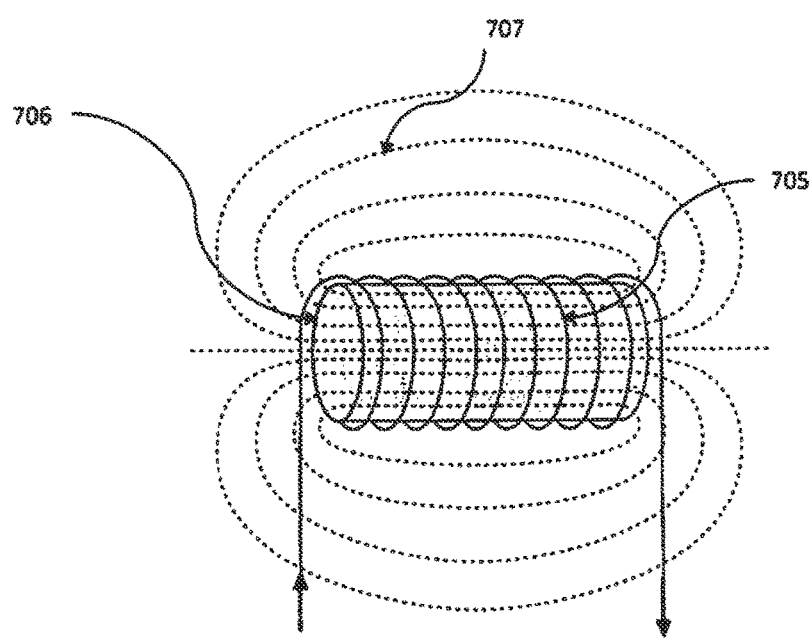
FIG. 11 displays a micro-coil that can generate intense magnetic field for repetitive magnetic transcranial stimulation.

FIG. 11 shows a magnetic coil 705. The size of these coils with the largest dimensions of on the order of 10 millimeters in size as have been fabricated by the laser direct write technology could provide very local stimulations. Other than laser direct write technology such coils could also be fabricated using MEMS technology or even non-micro fabrication technology. A current I passing through the coil will generate a magnetic field as shown by the field lines 707. As an example, the coil could have a diameter of 4 mm and a length of 1 cm with 70 turns. The brain cap of the invention may use arrays of these basic microcoils.

Figure 12A:
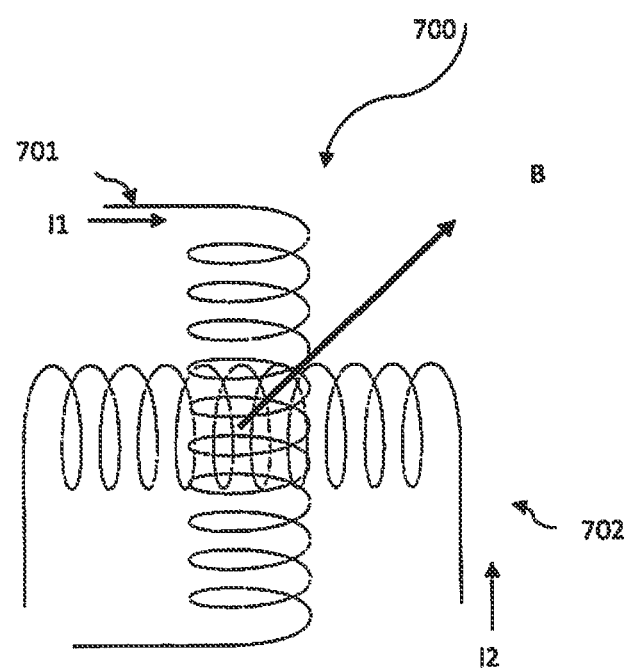
FIG. 12A displays a cross-coupled orthogonal microcoil that can generate magnetic field in any direction as well as varying such magnetic field in both intensity and temporally.

FIG. 12A shows a cross-coupled microcoil 700 with two coils 701, 702 orthogonal to each other (each coil 701, 702 is like coil 705 of FIG. 11). The cross coupling of the two coils 701, 702 allows the generation of a magnetic field B in any desired direction by simply varying the current I1, I2 of each coil independently without any physical movement of the coils themselves. Also, one can easily program the currents I1, I2 of the coupled coils to create a rotating magnetic field in either direction (clockwise and counterclockwise), thus providing flexibility to tailor the local field not only in intensity but also in direction as well as allowing temporal variations, such as a rotating field, other than the traditional pulsing used in the large coil for rTMS.

Figure 12B:
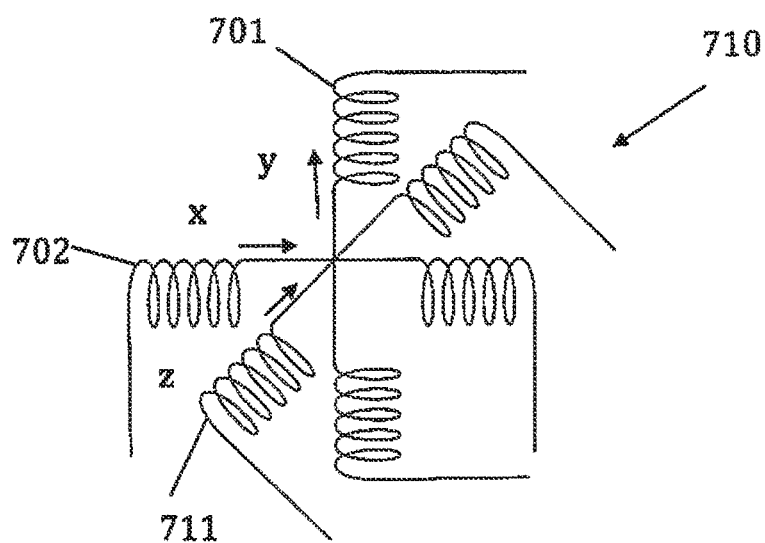
FIG. 12B is a schematic diagram of a 3-axis triple coil microcoil.

An extension of the cross coil concept is a 3-axis triple coil with a coil in each of the x, y, and the z directions as shown in FIG. 12B. The 3-axis cross coil 710 is made up of a pair of crossed coils 701, 702, as before, oriented along the x- and y-axes, along with an intersecting cross coil 711 oriented along the z-axis. This three dimensional 3-axis coil is essentially formed by adding a third coil orthogonal to the plane formed by the pair of crossed coils. This would allow one to control the field direction in any orientation. The brain cap of the invention more preferably uses the pairs of crossed coils or 3-axis triple coils to provide greater flexibility in the application of magnetic fields than single coils.

Figure 12C:
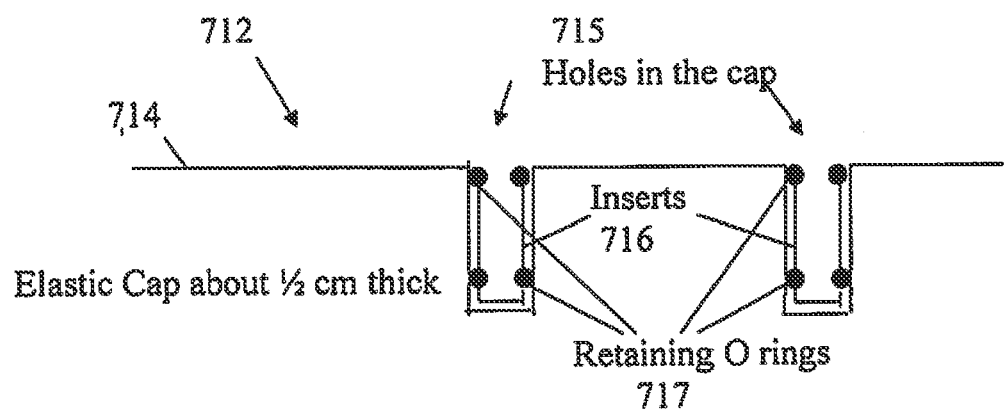
FIG. 12C shows a portion of a brain cap with holes and retaining cylinders for attaching the 3-axis microcoils of FIG. 12B.

Since the 3-axis coil is not substantially planar like the pair of crossed coils, but has a third coil extending orthogonally up and down from the two coil plane, the helmet must be modified so that the 3-axis coils can be mounted thereon. In one helmet design, shown in FIG. 12C, a brain cap or helmet 712 is made of a flexible cap 714 formed of a conforming elastic material about or somewhat greater than half the length of a coil (half of typically 1 cm) in thickness. Holes 715 are strategically positioned on the cap 714 with inserted locking cylinders (inserts) 716 made of non-magnetic material such as aluminum fitted tightly (possibly with glue) inside each hole 715. The holes 715 are designed to accept the half of the third coil that extends down toward the head. Any number of holes can be placed on the cap, including the maximum that would ever be used so that there is a generic cap. This generic cap can then be used to form a customized helmet by attaching 3-axis coils only at the positions desired for a particular application. Since there are more holes in the generic cap than the number of coils used for a particular application, there are many different options in how to "fill" the holes with the triple cross coils. Alternatively, the helmet can be made with just the desired holes for the number of coils to be used.

Figure 12D:
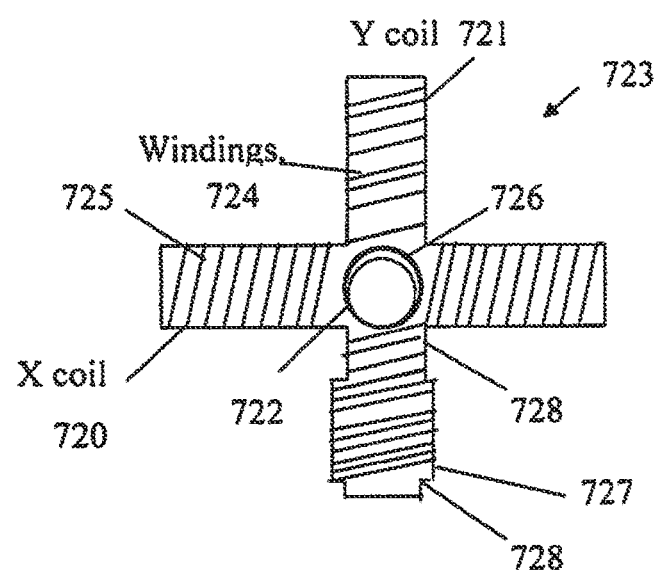
FIG. 12D is a side view of a 3-axis microcoil with a thicker central portion of one coil for locking into a helmet insert.
Figure 12E:
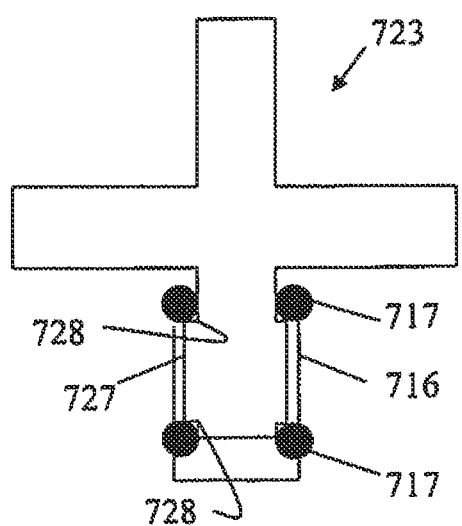
FIG. 12E shows a 3-axis microcoil inserted into a retaining locking cylinder.

Locking cylinders (inserts) 716 inserted in the holes 715 in the helmet 712 serve to lock the triple cross coils in place when one end of a coil is inserted inside a hole 715. A locking mechanism, e.g. two O-rings 717, secures the triple coil in place. FIG. 12D shows the three coils 720, 721, 722 of a triple cross coil 723 with windings 724, 725, 726. As shown, one half of coil 721 has a thicker central portion 727 within narrower portions 728 to allow the triple coil 723 to be locked into a helmet insert. In practice, all six halves of the three coils would have similarly shaped central portions, so that any coil half could be inserted into the insert. FIG. 12E shows the triple cross coil 723 (without the windings for clarity) inserted inside a locking cylinder 716 (without showing the brain cap). The O-rings 717 engage the narrower portions 728 of the coil that surround the wider central portion 727.

The densely populated cross coils can also be programmed to provide a magnetic field of a specific pattern over a broad area instead of the nonprogrammable single field coverage offered by a single big coil. A phase array arrangement of the coils could additionally provide penetration of the field at a focal spot deep inside the brain, such as the hippocampus regions which are important for Parkinson's disease, Alzheimer's disease, certain types of epilepsy, attention-deficit/hyperactivity disorder (ADHD), and other neurological ailments. Such deep penetration is achieved by a group of coils in which the relative phases of the respective signals feeding the coils are varied in such a way that the effective magnetic field pattern from the array is reinforced in a desired direction and suppressed in undesired directions. This is somewhat similar to the phase array structure used for a focal antenna in radar.

Figure 13:
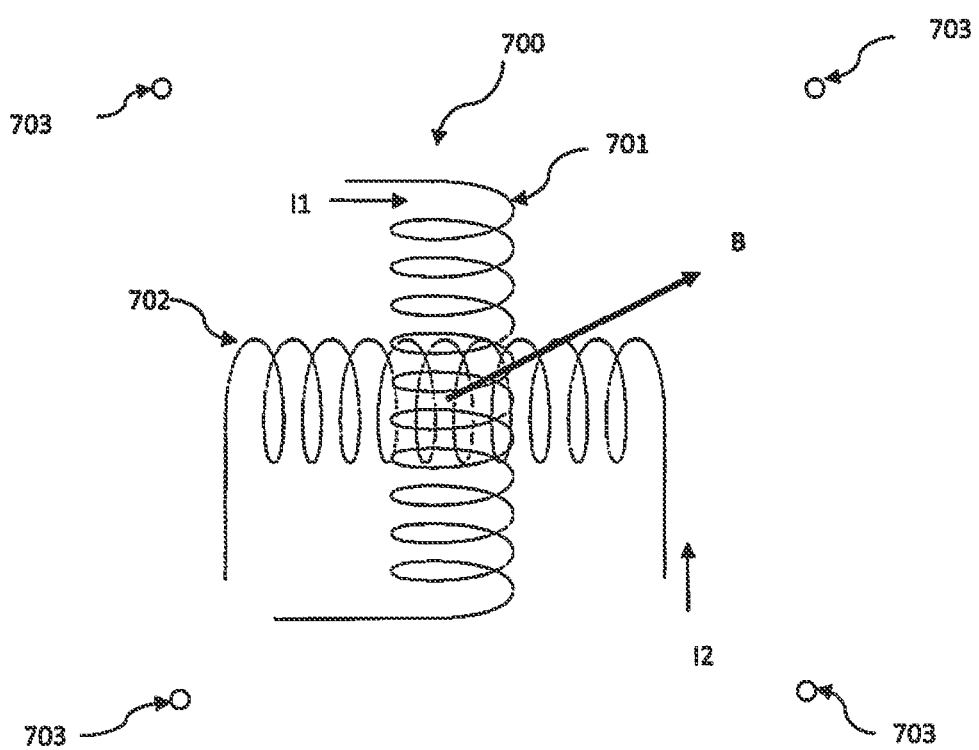
FIG. 13 displays the cross-coupled orthogonal microcoil together with four nearby brainwave sensors (micro-electrodes) to control the magnetic field of the microcoil.

This invention includes a special brain cap having an array of EEG microelectrodes and an array of magnetic field generating microcoils embedded in it, as shown in FIG. 9. FIG. 13 shows a cross-coupled microcoil 700 (made of a pair of microcoils 701, 702), as in FIG. 12A, at the center of and responding to EEG signals from four surrounding electrodes 703. The crossed microcoil 700 in FIG. 13 could be replaced with the 3-axis microcoil 710 in FIG. 12B or even by the single microcoil 705 of FIG. 11. At any particular location, the immediate surrounding electrodes or electrodes further away provide the necessary feedback signals to each microcoil to adjust all the relevant parameters (intensities, phases, pulse shapes, duty cycles, waveforms, and the pulsing frequencies of $I_1$ and $I_2$ going through the orthogonal coils 701, 702) that can affect the local magnetic field and the resulting eddy currents for that particular location. For such approach to be effective, certain proximity between the EEG electrodes and rTMS coils has to be observed. Current large scale systems simply prevent such close proximity arrangement; such local closed-loop structure between the electrodes and coils is not possible for the conventional rTMS system. The present invention with both the EEG microelectrodes and rTMS microcoils within the brain cap allows such realization.

The large number of coils in an array requires a system architectural design for power distribution, timing, clock and data distribution, waveform selection and synchronization, thermal management, individual element power gain control, and finally for compensation of the mutual inductance of the elements. The final packaging of the system will physically be in a three dimensional shape which will be hemispherical or hyperbolic ellipsoidal in nature. The three dimensional shape adds complexity to the requirements of the system's compensation for mutual inductance and control of the superposition of the inductors fields outputs.

Each element shall be identical in hardware design, and each may have a local lookup table to generate the required waveforms. Multiple identical units will greatly simplify manufacturing as well as part inventory for repair. The values for the lookup tables can be loaded prior to the start of the power output, or can be reloaded with new waveforms at the user's discretion. This will allow rapid testing and verification of candidate waveforms, and for compensation of the predicted mutual inductance of the elements. Timing and synchronization will be globally controlled from a central controller. Some efforts must be made in the areas of shielding the circuitry and the inductor elements from each other.

Lookup tables will give researchers and clinicians enormous latitude and flexibility to explore the impact of different waveforms, since only a few simple waveforms such as triangular and square wave have been used on conventional rTMS. Furthermore, for each individual patient, the waveform could be tailored to maximize the performance and the treatment outcomes.

Precise positioning is another significant advantage of this invention. Whereas the big coil requires a technician to carefully position the coil for possible optimal positioning both in respect to the location as well as to the coil-to-cortex separation, this is not necessary for the present invention. The soft brain cap somewhat similar to a swimming cap allows more precise coil-to-cortex separation whereas the density of the coils allows more precise positioning. The densely populated coils, each with its adjacent electrodes for feedback, eliminate any manual adjustment and also provide far more precise control and adaptation of the magnetic field for a particular shape and size of the patients' heads. Furthermore, the thicknesses of the skulls and the tissues can also affect the penetration of the field into the brains. In this invention, the EEG signals provide the guidance for the needed intensity to accomplish such tailored treatments. For conventional rTMS, the application of the same current to the magnetic field generating coil to different patients could result in different field intensity inside different patients' heads. This invention operates in a different set of parameters when compared with traditional rTMS. The magnetic field may induce an eddy current which produces electrical stimulations, in the polarization/depolarization of neurons, and through other means to alter neurons' electrical behaviors. It is the alternating magnetic field that induces the current. Typical rTMS uses extremely high magnetic fields, on the order of one Tesla, at a frequency typically less than 20 Hz. There is a safety concern because of reported induction of seizures. Also, typically rTMS fails to achieve deep penetration inside the brain, thus severely limiting the therapeutic effects.

Besides operating at high magnetic field, the present invention can also generate much lower magnetic fields, on the order of 1000 gauss or less, but with increased frequency of the alternating magnetic field to provide more effective or higher induced eddy current. Such an approach is inherently safer because of the lower magnetic field, simpler electronics, and less interference between the magnetic field and the brain sensor, such as the EEG measurements. Operating at the 100 Hz-10 KHz range and a field of 10-1000 gauss at the center for coils with suitable cores 706 of "amplifying magnetic medium" such as iron or similar high permeability materials (shown in FIG. 11), would be sufficient to induce a desirable outcome. Together with a dense array of coils instead of 1 or 2 coils, this ensures deep penetration for maximum therapeutic impact. Finally, the lower operating magnetic field will also minimize the heating effect on the coil, thus eliminating the possible need for cooling when a dense array of hundreds or more coils is used.

Deep brain stimulation allows stimulation regions deep inside the brain such as the STN area for Parkinson's disease. The array of microcoils of this invention could allow deep brain stimulation.

Figure 15:
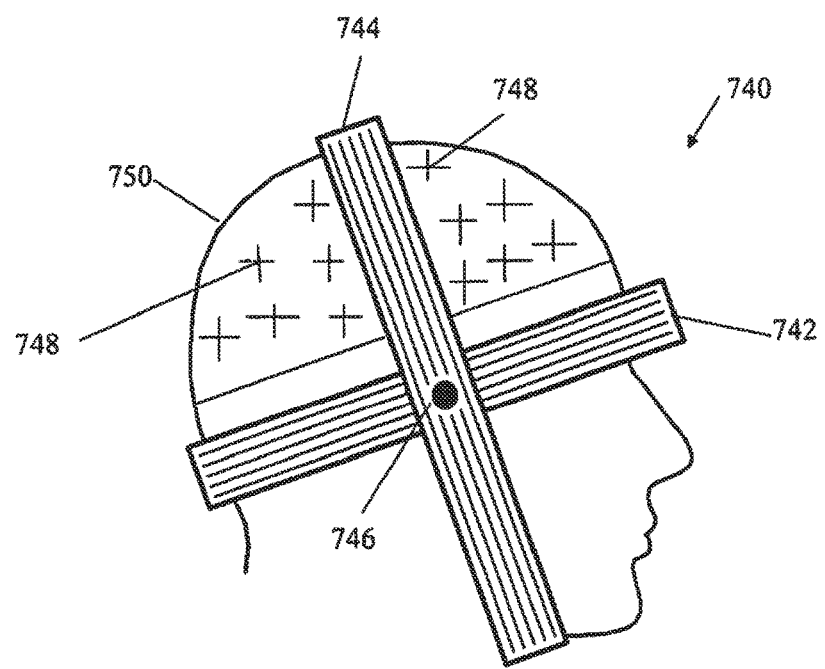
FIG. 15 shows a deep brain stimulation system having two large coils positioned around a person's head, in combination with a brain cap having an array of microcoils.

Another aspect of the invention that could achieve even deeper brain stimulation is to have two intersecting large coils in addition to the array of small coils. A non-invasive deep brain stimulation system 740 uses two intersecting large multi-turn coils 742, 744 each shaped like a head band—coil 742 is typically substantially horizontally orientated around the head at the forehead area and coil 744 is typically positioned substantially vertically to encircle the head from the top to just below the chin as seen in FIG. 15. The two coils 742, 744 act like a single large cross coil. By adjusting the currents of the two coils 742, 744, one can adjust the field direction to maximize the deep brain response. However, the two coils' relative positions could be changed through a pivot or rotating bearings 746 at the two intersecting points between the two coils 742, 744. By rotating one coil with respect to the other, the two coils could be adjusted to be at a 90 degree angle from each other as shown, or be adjusted to be almost parallel to each other when the angle is adjusted to the smallest, or to other angles in between. If one coil is smaller than the other, then the smaller one will fit or nest inside the larger, and they can be folded up into a parallel orientation.

While the two large coils 742, 744 could be used by themselves for some applications, in others they would be used in combination with an array of small cross coils 748 on a cap 750 placed on the top of the head, as previously described. While the large coils 742, 744 provide deep stimulation, the array of small coils 748 provides fine tuning. With its electronically controllable field directions creating both excitation and inhibition of various intensities at different surface locations simultaneously, the small coils 748 provide additional field settings, allowing many possible permutations for clinicians to create optimal treatments for various CNS diseases requiring deep brain stimulations. For example, the small coils can be set to cancel out most of the surface stimulations resulting from the two large coils, thus minimizing excitations at the surface cortex, or one can use them for fine adjustments to surface excitations to augment the deep penetration. Furthermore, as a research probe, such coil bands 742, 744 with an array of focal magnetic stimulation devices (microcoils 748) coupled with brain imaging would help in the study of fundamental neurological disorders, cognition, memory, and other CNS issues. If further coupled with tools for studying chemical neurobiology, such as magnetic resonance spectroscopic imaging, it will help provide a fuller picture to understand the brain.

Thus the invention includes a head-mounted non-invasive stimulation system with two large coil bands, about the size of the head, together with an array of small cross coils. The coils are driven by phased-array driving electronics and controlled by intuitive simulation software.

The next challenge is to determine the controlling parameters—the intensity level, the frequency, and the phase of the current for each of coil—especially since there can be as many as 1000 microcoils. The number of combinations could be a very large number and beyond the ability of a doctor to make all the adjustments. One solution is to use optimization theory to find the desired controlling parameters. At any moment, one has the measured responses from the brain sensors and the ideal responses, which can be either those from normal brains with no disorders or the brain responses of the patient when the disturbing conditions are not present. The goal is to control the levels, the frequencies, and the phases of the currents for the microcoils to achieve zero differences or close to zero differences between the measured responses and the target responses from the brain sensors or prior measured data from the patient. The simplest way is to use gradient descent for optimization but other more sophisticated algorithms could be used. The inclusion of an optimization software system would then provide an automatic means to achieve normalization, with the constraints that the controlling parameters, such as the current levels, are below the safety limits to avoid damaging the brain.

Besides rTMS, a possibly less intrusive approach is based on ear-point electrical stimulation. The advantage of using such ear-point stimulation is the simplicity in its implementation and the much lower cost when compared with using rTMS. A relatively simple low cost battery-powered electronic stimulator will do. Such a system similar to rTMS also allows closed-loop feedback from the EEG microelectrodes to the ear-point stimulations.

Yet another stimulation approach, somewhat in between rTMS and ear-point electrical stimulation, is the transcranial direct current stimulation (tDCS) which applies very weak electrical currents (1-2 mA) to modulate the activity of neurons in the brain.

Again, the stimulation or therapeutic system, whether using rTMS or ear-point stimulation or tDCS, is then coupled back to the brainwave monitoring system to complete the entire feedback system, allowing the brain signals to drive the amplitudes, phases, frequencies, and the patterns of the stimulations to restore the brain to its normal state. Such a self-regulating, on-demand, automatic system represents a different and novel therapeutic approach to assist patients such as those who have PTSD, depression, epilepsy, Parkinson's Disease, Autistic Spectral Disorders, insomnia, and other mental/neurological disorders to get a restful sleep at night as well as normalizing their brainwaves without possibly incurring the side effects of drugs and at the same time alleviating feelings of helplessness and loneliness in the middle of the night or other times when the psychotherapist is not available.

Since the magnetic fields or ear-point stimulations or the applications of tDCS are switched on only when they are required, such on-demand therapy will minimize possibly unnecessary treatments as in the cases of many pharmaceutical-based approaches. For example, this invention allows the possibility to treat pain perception instead of treating pain. Nerve block, a neurolytic procedure to destroy nerves to relieve cancer pain from certain organs such as from the pancreas, is well established. Thalamus, primary somatic area (SI), second somatic area (SII), insular cortex (IC), prefrontal cortex (PFC), cingulated cortex, and parietal cortices are pain source areas. As a result, one can use neurological stimulations to act on these areas to block pain without severing the nerves. If pain is not felt by the patient, stimulation, such as by magnetic field, can be terminated. Such approach is not possible for pharmaceutical treatment because medications typically have long half-lives; for example, morphine has a half-life of up to 7 hours, and thus their impact and the associated side effects will persist even after the pain is gone because of the lingering drug impact. An advantage of the present invention is that it does away with such negative impact. Furthermore, the body adapts to the impact of narcotic drugs and thus often requires increasing dosage over time to alleviate the pain. This often leads to the complication and the expense in adding anti-nausea drugs to the pharmaceutical regimen. This invention is likely to lead to minimizing or eliminating the need to administer such anti-nausea medications.

Yet another pain control procedure using the invention is to pick up the pain signatures from the brainwaves and use the signatures to control the analgesic delivery. One such example is based on the principle of iontophoresis. Iontophoresis works by delivering a positively charged drug across the skin by placing a cationic drug at the positive electrode where it is repelled and then attracted towards a negative electrode placed elsewhere on the body. (Delivery of positively charged compounds is generally easier than negatively charged compounds as the skin itself possesses a net negative charge.) By applying a voltage, one can then control the amount of drug delivery. One such commercial pain product is the Fentanyl HCl iontophoretic transdermal system. By connecting such a system to the invention, one can let the brainwave patterns corresponding to the pain level deliver the necessary drug dosage and only when needed. Again, the advantages are that less pain killer and thus less anti-nausea medication will be needed. Subjective pain intensity is influenced by an individual's mental condition. Attention has been shown to alter experimental pain and thus can play an important role in the treatment of clinical pain. Recent research has shown that pain perception can be affected by attention distraction. As a result, when a patient has a visitor who cheers him up, his perception of pain is less and the brainwave pattern will reduce the amount of drug delivery. Similarly, the system can be hooked to a morphine drip system to supply morphine only when pain is perceived and it is within the dosage safety.

Yet another method is to apply the stimulations at the sites of the pain such as the back for back pain or to jaw area for toothache.

While there are multiple approaches to deal with pain as mentioned above, similarly there are more than one way to deal with diseases such as the Parkinson's Disease and other diseases. For example, instead of using cleaned-up EEG signals to guide the stimulation treatments as stated earlier, one can directly use the degree of tremor of a patient to guide the amount of stimulation needed to treat the tremor of a Parkinson's patient.

In daytime, the patient has the choice to continue using such an "on-demand" system or if the patient prefers not to have any external stimulation, one can use another non-pharmacotherapy technique such as neurofeedback for retraining aberrant brainwaves as has been used with some success in helping PTSD and epileptic patients.

In addition, because of the ability of this invention to create very localized stimulation provided by these densely populated microcoils and the availability of densely populated clean EEG measurements with unprecedented spatial resolution after or during rTMS applications, one can use this non-invasive combination as a powerful diagnostic tool to localize and to reveal specific regional dysfunctions that could be the cause or the triggering event for many mental and neurological disorders. For example, currently there are no medical tests for diseases such as Parkinson's disease (PD) and Alzheimer's disease (AD). The test, the Uniform Parkinson's Disease Rating Scale, is subjective and thus not really scientific. This invention possibly allows a different approach to diagnose these diseases. Furthermore, rTMS applied to motor cortical regions has also been shown to improve symptoms in PD and modulate motor cortical excitability. Specifically, striatal dopamine release induced by repetitive transcranial magnetic stimulation of the human motor cortex has been demonstrated and thus has consequences in the treatments of PD, schizophrenia and drug addiction. Also, prefrontal application of rTMS has shown quantitatively similar striatal dopaminergic effects to those associated with the administration of d-amphetamine, a psychostimulant known to increase synaptic dopamine. Thus the use of rTMS has been shown to duplicate the effect of a certain pharmaceutical drug. But since d-amphetamine treatment with monoamine oxidase (MAO) inhibitors is strongly contraindicated, treatment with d-amphetamine should also be avoided in patients suffering from physical health conditions including cardiovascular disease, hypertensive disease, hyperthyroidism, glaucoma and anorexia. As a result, the use of rTMS could be a vital substitute for d-amphetamine treatment to those patients who also have the above mentioned health conditions. In addition, sleeping disorder which is common among PD patients, can be helped with rTMS and thus by this invention. rTMS also seems to be a noninvasive alternative treatment for PD patients with lower urinary track dysfunction. This powerful, non-invasive tool could also help to identify surgical candidates and provide additional information for neurologists and neurosurgeons for tailored treatments. In addition, such a system can be an extremely powerful cognitive investigation tool for the study of the human brain and the cognition system because the cleaned up real time EEG allows dynamical tracking of the brain processing whereas the poor temporal resolutions of positron emission tomography (PET) and the functional magnetic resonance imaging (fMRI) tools, on the order of minutes, could not.

One application of the large coil system 740 in combination with the brain cap 750, as shown in FIG. 15, is to induce cortical effective connectivity disruption, resulting in loss of consciousness. Thus the invention could be used to induce anesthesia. Because of the location of the thalamus deep inside the brain, interruption of activities there requires deep brain stimulation. The combination of the large coils alone, or in combination with the array of microcoils, could non-invasively impact the thalamus as well as its connection to the cerebral cortex, thus interrupting signals relating to sensation and motor signals. Furthermore, the EEG system with its noise removal algorithm coupled with the treatment system could be used to induce anesthesia and at the same time monitor the degree of consciousness, resulting in inducing anesthesia adaptively or having it tailored to an individual.

Such a brain cap could also have many other non-medical applications such as cognitive enhancement. rTMS has been demonstrated to enhance language processing and is capable of transitorily and positively influencing brain function and cognition among elders with memory complaints. Another application of this invention is to sustain covert military missions by keeping operators in a heightened alert mode through appropriate stimulations so as to finish enduring and dangerous missions without suffering from interruptions and deteriorating performances of the operators due to the length of the mission leading to possible mission failures. For example, Modafinil (Provigil/Alertec) is a stimulant drug acting as a "wakefulness promoting agent". It has been used on certain U.S. Air force missions to keep soldiers alert for extended numbers of hours but it has side effects. It may induce severe dermatologic reactions requiring hospitalization. Severe adverse reactions include erythema multiforme, Stevens-Johnson syndrome, toxic epidermal necrolysis, angioedema and multi-organ hypersensitivity reactions, and drug rash with eosinophilia and systemic symptoms involving adult and pediatric patients. The present invention could promote wakefulness without possibly the pharmaceutical induced side effects. Soldiers equipped with the brain caps may also be able to stabilize their neurotransmitter levels and possibly their cognitive functions in the event of manifestations of seizures due to a biochemical attack. This could happen if their protective suits fail because of defects or improper suiting up due to limited advance notice. The brain uses different combinations of regions for processing different types of information. For example, English and Chinese languages utilize different brain systems and they are different from those processing symbolic languages. Knowing the particular regions for certain specific learning allows stimulation of those particular regions to potentially speed up the learning process. This is especially true for learning highly complicated, multi-dimensional, informational systems such as those faced by intelligence analysts. This invention also has major implications in various investigations such as deception analysis and could be far superior to polygraph testing not only because of improved accuracy but also because it will reveal not only deception but the kinds of deceptions for the subjects under investigation because different types of deceptions activate different parts of the brain. This invention also can analyze how the brain receives and processes instructions and information when new teaching tools, techniques, and/or materials, and/or methodologies are introduced; as a result, one can compare the effectiveness of the different teaching tools and/or methodologies. This will result in better teaching in the classrooms as well as allowing individualized teaching based on the differences in responses from different students; thus it could impact our continually deteriorating educational system. Such a brain-based monitoring system could also be the base for various types of brain-based control systems such as a brain-computer-interface or BCI for quadriplegics and a new generation of brain-based video game controls as well as neuro-prostheses for better control of artificial limbs for amputees to regain mobility because a control system based on invasively implanted brain electrodes might not be a long-term realistic solution because the body views the implants as foreign objects, and will degrade the signals as a function of time.

The invention has many other applications than just the medical ones. One example is to use part of this invention for video game control. Instead of the old fashioned joy stick approach, one can use this brain cap to "read" the "mind" of the gamer to control the characters and their accessories in a video game. To accomplish this, again the brainwave signals are collected through the braincap worn by a gamer. While possibly not all the microelectrodes are needed for such an application, the availability of large spatial and dense coverage of the microelectrodes means that one can expand the capabilities when the gamer becomes more sophisticated. The signals are then cleaned up to ensure that noisy signals do not get misinterpreted. Instead of a database of signatures corresponding to different neurological disorders, a database of signatures corresponding to actions such as walk forward, move backward, make a left turn, stop, grip the object in front, peek around the wall, shoot, and open the "magic box" are used. Similarly, the brainwave signatures are then matched to identify the appropriate actions using supervised neural networks, unsupervised methods such as SOM, and vector quantization as stated before. These actions will then be translated to electrical signals sent back to the computer just like the joy stick sending information back to control the game. Such a device can then readily be adapted for the use of a neuro-prosthesis or for a fighter pilot to control his/her actions in front of a forever-increasing and overwhelming amount of information displayed in the cockpit. Another example is dictation because speech recognition still has some major shortcomings. For example, one may prefer not to dictate on a train or a subway or while walking down the street or in a library. With this invention, a database of brainwave signatures corresponding to commonly used words, phrases and expression can be created to translate the thought process into writing since the first 25 most commonly used words are in 33% of everyday writing and the first 100 words appear in 50% of adult and student writing, and finally the first 1,000 words are used in 89% of everyday writing. Thus a 1,000-word library could be useful for "writing" simple notes.

The invention also includes methods and apparatus for treating medical conditions using only a microcoil based treatment system, without the microelectrodes or other sensor elements for detecting signals and the signal processing method and apparatus for cleaning up the signals. For some conditions, it may not be necessary to measure brainwaves to determine an abnormal condition requiring treatment. For example, a person may be known to be depressed. In these cases, a helmet with only microcoils may be placed on the head of the patient, and rTMS signals applied to the patient for a period of time.

One application where sensors may not be needed is for weight control. Food craving comes from neurologically initiated desire for food. By reducing such cravings, weight reduction could be possible. Performing rTMS over the rDLPC region of the brain decreases desire for food in humans. During food craving episodes for humans, as evident through MRI, craving-specific activation was seen in three regions of the brain: the hippocampus, insula, and caudate. These regions are located deep inside the brain. Thus there may be different types of food cravings originated from different regions of the brain. The brain cap of the invention, either alone or in combination with the large coils shown in FIG. 15, could be used to inhibit activities in all these regions and thus reduce desires for food. Another application where sensors may not be needed is for treating addiction, e.g. smoking or drugs.

Figure 16:
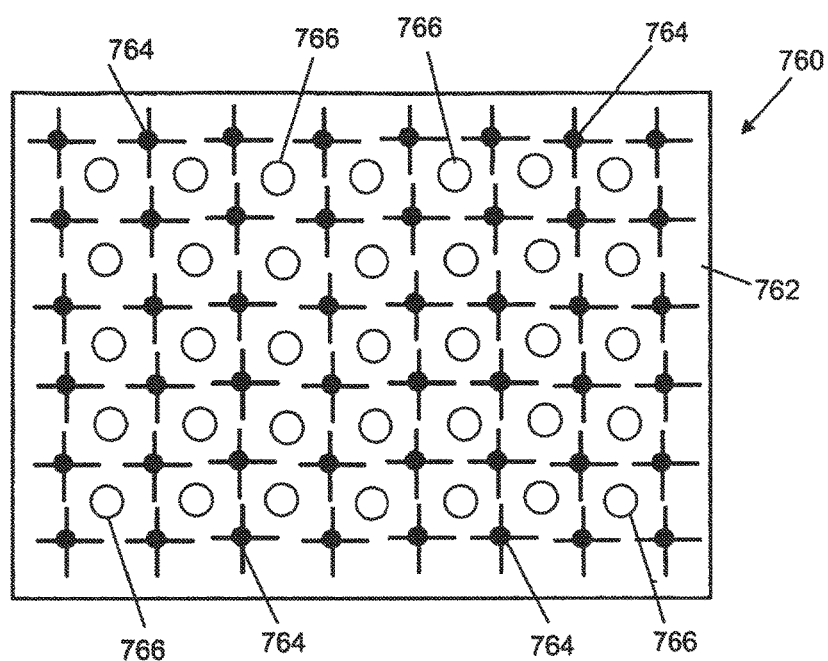
FIG. 16 shows a pad or band with an array of microcoils.

While the invention has been described as being directed to mental or neurological conditions, it may also be applied to other than brain based conditions. An array of microcoils, whether single coils, crossed pairs of coils, or crossed 3-axis triple coils, can be placed on a treatment device other than a brain cap or helmet. As shown in FIG. 16, a therapeutic device 760 is formed of a pad or band or other substrate 762 on which a plurality of microcoils 764 is placed. Optionally, a plurality of micro-sensor elements 766 may also be placed on pad or band or other substrate 762. Pad or band or other substrate 762 may then be placed or wrapped around other parts of the body than the head, e.g. neck, chest, abdomen, arm, leg, and the microcoils 764 used to apply therapeutic treatment. Microsensors 766 could be used to detect signals which could be processed as described previously to provide feedback to control the therapy.

One possible application of the invention that could use different treatment articles than a brain cap and may not use microsensors is hypothermia (HT) or heat treatment of cancer tumors. In local hyperthermia, heat is applied to a small area, such as a tumor, using various techniques that deliver energy to heat the tumor. Different types of energy may be used to apply heat, including microwave, radiofrequency, and ultrasound. However, these techniques could be problematic for tumors deep inside the body and also localization could be a problem. Using the small cross coils of the invention to generate magnetic fields could achieve more localized treatment. A pad or other article containing a plurality of microcoils would be placed on the body over the tumor, and current flowed through the microcoils. There are two methods for the transfer of energy. Hyperthermia energy could come from the magnetic field itself or from the eddy current induced by the magnetic field or a combination of the two. Furthermore, the invention could be used in nanoparticle-mediated thermal therapy, in which nanoparticles are injected into the tumor to facilitate heating. By using appropriately designed nanomaterial, one could further localize treatments by making the nanomaterial more adsorbent to the magnetic field energy or to the electric field energy produced by the microcoils, or the nanomaterials can be fabricated with better efficiency in converting the electric or magnetic energy into thermal energy. Sensors would not generally be used for such cancer treatment since there is no immediate feedback, but temperature sensors might be used to better control the HT process.

Another application is as a cardiac defibrillator. The invention produces magnetic fields to penetrate the skin and muscles, resulting in induced eddy current inside to shock the heart, thus minimizing direct current related discomfort, wet skin issues, excessive hair problems, etc. Because a magnetic field is used and current is induced, no external current path return is necessary. A pad with an array of microcoils will be placed over the heart and current flowed through the coils to produce the fields.

While particular operational sequences, materials, and particular embodiments have been described and/or illustrated, such are not intended to be limiting. Modifications and changes may become apparent to those skilled in the art, and it is intended that the invention be limited only by the scope of the appended claims.

I claim:

1. A method for processing brainwave signals of a patient having a neurological or mental disorder, the method comprising:
   receiving, by one or more processors, a brainwave signal obtained by a device coupled to a patient, the brainwave signal containing noise;
   performing, by the one or more processors, an n-level decomposition of the brainwave signal into wavelet components of different scales to separate the brainwave signal from the noise;
   for each individual wavelet component among the wavelet components of different scales, inputting, by the one or more processors, the individual wavelet component into a corresponding compression module to squeeze out the noise from the individual wavelet component in a decomposed domain, wherein the compression module is self-supervised and has been trained by creating an output behavior of the compression module that closely matches an input behavior of the compression module;
   performing, by the one or more processors, an inverse decomposition on outputs from the compression modules to recover a clean brainwave signal in a time domain; and
   causing, by the one or more processors, physiological stimulation of the patient with signals generated based on the neurological or mental disorder of the patient as determined by comparing the clean brainwave signal to at least one of a plurality of normal or abnormal brainwave signals stored in a database, wherein each abnormal brainwave signal is indicative of a neurological or mental disorder.

2. The method of claim 1, wherein the n-level decomposition is a wavelet decomposition into different scales, or a multi-resolution pyramid decomposition into different scales.

3. The method of claim 1, wherein the compression modules are vector quantizers or auto-associative neural networks.

4. The method of claim 1, wherein the method is implemented in a data processing or analyzing system, or as firmware or hardware that includes an application-specific integrated circuit (ASIC), a full-custom chip, a digital signal processing (DSP) chip, or a graphic processor chip (GPC) for real time processing.

5. The method of claim 1, wherein the n-level decomposition is a multi-resolution pyramid scheme performing successive averaging to obtain smoother scales as decomposed signal moves up the pyramid and scales with lower resolutions.

6. The method of claim 5, wherein the successive averaging is performed by multiple neural networks.

7. The method of claim 5, further comprising:
performing a preliminary denoise process by eliminating components from lower parts of the multi-resolution pyramid.

8. The method of claim 5, wherein the n-level decomposition using artificial neural networks in the multi-resolution pyramid scheme and the compression modules provide resilience in the performance of the process of the signal through a flexibility of denoising in the multi-resolution pyramid scheme.

9. The method of claim 2, wherein the decomposed components include a highest-order smooth component and additional rough components.

10. The method of claim 9, further comprising:
performing a preliminary denoising process by retaining only the smoothest component thus allowing quick assessment of signal of interest to determine whether further processing is needed.

11. The method of claim 9, further comprising:
performing a preliminary denoising process by eliminating a plurality of lower-level rough components from the wavelet stage or the multi-resolution pyramid scheme resulting in performing both decomposition for subsequent neural network denoising and early denoising function in one single procedure.

12. The method of claim 9, further comprising:
performing a preliminary denoising process by eliminating a plurality of lower-level components or selective rough components, enabling progressive signal processing which selectively trades off between extracted signal quality and processing complexity and speed; wherein the preliminary denoising process impacts real-time processing with capability of adding more of eliminated components to improve signal quality.

13. The method of claim 1, wherein the n-level decomposition and the compression modules provide resilience to performance of the overall process of the signal by permitting suboptimal denoising in the decomposition stage that may be compensated in a subsequent compression stage.

14. The method of claim 1, wherein the brainwave signal includes an Electroencephalography (EEG) signal, an infrared (IR) signal, a magnetometer signal from an alkali vapor magnetometer or a superconducting quantum interference device (SQUID), or a signal from other sensor that can sense brain activities.

15. The method of claim 1, wherein the decomposition and compression allow for efficient data storage because relatively intense noise over trace signals occupying more storage space has been removed.

16. The method of claim 1, wherein achieving optimization control is through gradient descent.

17. The method of claim 1, wherein the brainwave signal is one dimension of a multi-dimensional signal that has data of multiple dimensions.

18. A method for processing brainwave signals for treating a patient having a neurological or mental disorder, comprising:

receiving, by one or more processors, a brainwave signal obtained by a cap or pad placed on a head of the patient, the brainwave signal containing noise, and the cap or pad including a plurality of microelectrodes or microsensors for measuring the brainwave signals from the patient and a plurality of coils for applying therapeutic treatment to the patient;

performing, by the one or more processors, an n-level decomposition of the brainwave signal into components of different scales;

for each individual component among the components of different scales, inputting, by the one or more processors, the individual component into a corresponding compression module to squeeze out the noise from the individual component in a decomposed domain, wherein the compression module is self-supervised and has been trained by creating an output behavior of the compression module that closely matches an input behavior of the compression module;

performing, by the one or more processors, an inverse decomposition on outputs from the compression modules to recover a clean brainwave signal in a time domain; and causing, by the one or more processors, physiological stimulation of the patient via the plurality of coils with signals generated based on the neurological or mental disorder of the patient as determined by comparing the clean brainwave signal to at least one of a plurality of normal or abnormal brainwave signals stored in a database, wherein each abnormal brainwave signal is indicative of a neurological or mental disorder.

19. The method of claim 18, further comprising:
supplying power to the microelectrodes and microsensors of the cap using radiofrequency (RF) coupling to operate the cap without using a battery.

20. The method of claim 18, wherein the coils of the cap are operated in synchrony as a phased array for providing deep brain stimulation.

21. The method of claim 18, wherein the plurality of coils work at lower power in tandem in a phased-array arrangement to minimize chance of heating up electrodes and electronic circuits.

22. The method of claim 18, wherein the microelectrodes and microsensors are in close proximity to treatment devices to allow effective local feedback for therapy.

23. The method of claim 18, wherein the coils of the cap operate at high magnetic fields on the order of one Tesla at a frequency of less than 20 Hz.

24. The method of claim 18, wherein the coils of the cap operate at low magnetic fields on the order of 1000 gauss or less, at a frequency of from 100 Hz to 10 KHz.

25. The method of claim 18, wherein the coils of the cap include large coil bands or small cross coils or a combination thereof that work in tandem and are driven by phased-array driving electronics to improve deep brain stimulation.

26. The method of claim 18, wherein the transcranial direct current stimulation (tDCS) system or magnetic transcranial stimulation (MRS) with coils for the cap include large coil bands or small cross coils of a combination thereof that work in tandem to function as nerve block for pain treatment without surgically severing nerves.

27. The method of claim 26, wherein the nerves are in a primary somatic area (SI), a second somatic area (SII), an insular cortex (IC), a prefrontal cortex (PFC), or a parietal cortices.

28. The method of claim 18, wherein the cap or coating of the coils includes material with low thermal conductivity to reduce heat damages to the skin.

29. The method of claim 18, wherein the cap or pad includes soft body-conforming material to allow precise coil-to-skull or coil-to-body separation and spatial positioning to give better control and adaptation to different head shapes or head sizes or body shapes or body sizes.

30. A method for processing body-generated signals of a patient having a disorder, the method comprising:
   receiving, by one or more processors, a body-generated signal obtained by a device coupled to a patient, the body-generated signal containing noise;
   performing, by the one or more processors, an n-level decomposition of the body-generated signal into components of different scales to separate the body-generated signal from the noise;
   for each individual component among the components of different scales, inputting, by the one or more processors, the individual component into a corresponding compression module to squeeze out the noise from the individual component in a decomposed domain, wherein the compression module is self-supervised and has been trained by creating an output behavior of the compression module that closely matches an input behavior of the compression module;
   performing, by the one or more processors, an inverse decomposition on outputs from the compression modules to recover a clean body-generated signal in a time domain; and
   causing, by the one or more processors, physiological stimulation of the patient with signals generated based on the disorder of the patient as determined by comparing the clean body-generated signal to at least one of a plurality of normal or abnormal body-generated signals stored in a database, wherein each abnormal body-generated signal is indicative of a disorder.

31. The method of claim 30, wherein the body-generated signal is an Electroencephalography (EEG) signal, an electrocardiogram (EKG) signal, or an internal emission signal from a human body.

32. The method of claim 30, wherein the body-generated signal is induced when the patient's body responds to external stimulation, the external stimulation being X-ray, magnetic field, radioactive-nuclide treatment, microwave, radio-frequency wave, ultrasound, or a stimulation that provokes a human body to response.

* * * * *